US012781246B2

(12) United States Patent
Yamaguchi et al.

(10) Patent No.: US 12,781,246 B2
(45) Date of Patent: Nov. 3, 2026

(54) METHOD FOR PRODUCING TRANS-POLYISOPRENOID, VECTOR, TRANSGENIC ORGANISM, METHOD FOR PRODUCING PNEUMATIC TIRE, AND METHOD FOR PRODUCING RUBBER PRODUCT

(71) Applicants: SUMITOMO RUBBER INDUSTRIES, LTD., Kobe (JP); TOHOKU UNIVERSITY, Sendai (JP)

(72) Inventors: Haruhiko Yamaguchi, Kobe (JP); Yukino Miyagi Inoue, Kobe (JP); Toru Nakayama, Sendai (JP); Seiji Takahashi, Sendai (JP)

(73) Assignees: SUMITOMO RUBBER INDUSTRIES, LTD., Kobe (JP); TOHOKU UNIVERSITY, Sendai (JP)

( * ) Notice: Subject to any disclaimer, the term of this patent is extended or adjusted under 35 U.S.C. 154(b) by 318 days.

(21) Appl. No.: 18/683,070

(22) PCT Filed: Aug. 19, 2022

(86) PCT No.: PCT/JP2022/031290

§ 371 (c)(1),
(2) Date: Feb. 12, 2024

(87) PCT Pub. No.: WO2023/037842

PCT Pub. Date: Mar. 16, 2023

(65) Prior Publication Data

US 2024/0401087 A1 Dec. 5, 2024

(30) Foreign Application Priority Data

Sep. 10, 2021 (JP) ................................ 2021-147831

(51) Int. Cl.

| | |
|---|---|
| ***C12P 5/00*** | (2006.01) |
| ***B60C 1/00*** | (2006.01) |
| ***C08L 21/00*** | (2006.01) |
| ***C12N 9/10*** | (2006.01) |
| ***C12N 11/02*** | (2006.01) |

(52) U.S. Cl.

CPC ................ *C12P 5/007* (2013.01); *B60C 1/00* (2013.01); *C08L 21/00* (2013.01); *C12N 9/1085* (2013.01); *C12N 11/02* (2013.01)

(58) Field of Classification Search

CPC combination set(s) only.
See application file for complete search history.

(56) References Cited

U.S. PATENT DOCUMENTS

| | | | | |
|---|---|---|---|---|
| 2010/0218272 | A1 | 8/2010 | Nakazawa et al. | |
| 2019/0376093 | A1 | 12/2019 | Sakurai et al. | |
| 2023/0002792 | A1* | 1/2023 | Yamaguchi .......... | C12N 9/1085 |

FOREIGN PATENT DOCUMENTS

| | | | |
|---|---|---|---|
| EP | 3 992 295 | A1 | 5/2022 |
| JP | 5645366 | B2 | 12/2014 |
| JP | 5870464 | B2 | 3/2016 |
| JP | 2016-93186 | A | 5/2016 |
| JP | 6090700 | B2 | 3/2017 |
| JP | 2018-99100 | A | 6/2018 |
| JP | 2021-13365 | A | 2/2021 |
| JP | 2021-80204 | A | 5/2021 |

OTHER PUBLICATIONS

Kajiura et al., "Structure-function studies of ultrahigh molecular weight isoprenes provide key insights into their biosynthesis," Communications Biology, vol. 4, No. 215, XP093093924, Feb. 16, 2021, pp. 1-13.
Miwa et al., "In vitro biosynthesis of isoprenoid polymers by trans-prenyltransferases identified from Manilkara zapota," Japan Society for Bioscience, Biotechnology, and Agrochemistry, Mar. 5, 2021, 2 pages total, with English translation.
International Search Report (PCT/ISA/210) issued in PCT/JP2022/031290, dated Oct. 13, 2022.
Written Opinion of the International Searching Authority (PCT/ISA/237) issued in PCT/JP2022/031290, dated Oct. 13, 2022.

* cited by examiner

*Primary Examiner* — Tekchand Saidha
(74) *Attorney, Agent, or Firm* — Birch, Stewart, Kolasch & Birch, LLP

(57) ABSTRACT

The present disclosure aims to provide a method for producing a trans-polyisoprenoid (trans-1,4-polyisoprene) with a molecular weight of more than $10^5$ in an enzymatic manner. The present disclosure relate to a method for producing a trans-polyisoprenoid, which includes binding to a lipid membrane in vitro a trans-prenyltransferase (tPT) family protein capable of producing a product with a molecular weight of $10^4$ or more when not bound to any lipid membrane.

7 Claims, 5 Drawing Sheets

Specification includes a Sequence Listing.

METHOD FOR PRODUCING TRANS-POLYISOPRENOID, VECTOR, TRANSGENIC ORGANISM, METHOD FOR PRODUCING PNEUMATIC TIRE, AND METHOD FOR PRODUCING RUBBER PRODUCT

REFERENCE TO ELECTRONIC SEQUENCE LISTING

The application contains a Sequence Listing which has been submitted electronically in .XML format and is hereby incorporated by reference in its entirety. Said .XML copy, created on Aug. 19, 2024, is named "5051-0570PUS1.xml" and is 53,658 bytes in size. The sequence listing contained in this .XML file is part of the specification and is hereby incorporated by reference herein in its entirety.

TECHNICAL FIELD

The present disclosure relates to a method for producing a trans-polyisoprenoid, a vector, a transgenic organism, a method for producing a pneumatic tire, and a method for producing a rubber product.

BACKGROUND ART

At present, natural rubber (a polyisoprenoid) for use in industrial rubber products may be obtained by cultivating rubber-producing plants, such as para rubber tree (*Hevea brasiliensis*) of the family Euphorbiaceae or Indian rubber tree (*Ficus elastica*) of the family Moraceae. Such natural rubber is a polyisoprenoid (cis-natural rubber) in which isoprene units are linked in a cis configuration. Other polyisoprenoids in which isoprene units are linked in a trans configuration, trans-polyisoprenoids (trans rubber), also exist in nature.

A few species of plants in nature, such as *Eucommia ulmoides* belonging to the family Eucommiaceae of the order Eucommiales, a high deciduous tree native to China, are known to produce trans-polyisoprenoids (trans rubber). The trans-polyisoprenoids can be extracted from the seeds or pericarp tissue of *Eucommia ulmoides*. They can also be chemically synthesized. Such trans rubber has different characteristics from cis-natural rubber and has been used in crack-resistant golf balls, materials to fill dental cavities to be treated, etc.

The chemically synthesized trans-polyisoprenoids do not have a trans content of 100% but contain about 1.2 to 4% of cis linkages. They also have a molecular weight of about 250,000. It is very difficult to synthesize those having an ultra-high molecular weight of 1,000,000 or more. Moreover, their chemical synthesis requires a supply of raw materials, including petroleum-derived raw materials, and this is hardly an environmentally friendly procurement process.

Meanwhile, a trans-polyisoprenoid extracted and purified from the plant *Eucommia ulmoides* is a polyisoprenoid having a weight average molecular weight of about $1.8\times10^6$ in which at least 99% of the units of the straight chain are trans-linked. It has been used as eucommia elastomer.

Trans-polyisoprenoids (trans rubber) are biosynthesized in plants by addition polymerization of isopentenyl diphosphate (IPP) to a starting substrate such as farnesyl diphosphate (FPP) or geranylgeranyl diphosphate (GGPP) and has a trans-1,4-polyisoprene structure. Due to this structure, trans-prenyltransferase (tPT) is considered to be involved in the biosynthesis of trans rubber.

Patent Literatures 1, 2, and 3 have reported long-chain trans-prenyl diphosphate synthase genes which are trans-prenyltransferases derived from *Eucommia ulmoides*, as well as methods of using these genes to grow transgenic plants and then collecting trans-1,4-polyisoprenes.

However, only a range of $10^4$ to $10^5$ has been reported in the reported examples of transgenic tobacco. No production of polymers of more than $10^5$ has been achieved.

CITATION LIST

Patent Literature

Patent Literature 1: JP 6090700 B
Patent Literature 2: JP 5870464 B
Patent Literature 3: JP 5645366 B

SUMMARY OF DISCLOSURE

Technical Problem

The present disclosure aims to solve the above-described problem and provide a method for producing a trans-polyisoprenoid (trans-1,4-polyisoprene) with a molecular weight of more than $10^5$ in an enzymatic manner.

The present disclosure also aims to solve the above-described problem and provide a vector which, when introduced into an organism by gene recombination techniques, can produce a trans-polyisoprenoid with a molecular weight of more than $10^5$ in an enzymatic manner. The present disclosure also aims to provide a transgenic organism into which the vector has been introduced and a method for producing a trans-polyisoprenoid with a molecular weight of more than $10^5$ in an enzymatic manner using the transgenic organism.

Solution to Problem

With the aim of solving the problem, the present inventors isolated two genes with two conserved motifs for trans-prenyltransferases from *Manilkara zapota*, a plant that biosynthesizes a trans-1,4-polyisoprene.

It has been found that one of the two isolated trans-prenyltransferases (tPT1 derived from *Manilkara zapota*, the nucleotide and amino acid sequences represented by SEQ ID NOs:1 and 2, respectively) has activity and the ability to synthesize a product with a molecular weight of about $10^3$ when not bound to any lipid membrane. It has been discovered that the other trans-prenyltransferase (tPT2 derived from *Manilkara zapota*, the nucleotide and amino acid sequences represented by SEQ ID NOs:3 and 4, respectively) with the full-length sequence exhibits no activity when not bound to any lipid membrane, but deletion of the membrane-binding peptide domain (the nucleotide sequence of tPT2 derived from *Manilkara zapota* from which the membrane-binding peptide domain has been deleted (MztPT2ΔN) is represented by SEQ ID NO:6) allows it to exhibit the ability to synthesize a product with a molecular weight of about $10^4$ when not bound to any lipid membrane.

As a result of further studies, it has been discovered that, when the trans-prenyltransferase having the ability to synthesize a product with a molecular weight of about $10^4$ is expressed in the presence of a lipid membrane while containing a membrane-binding peptide domain, it exhibits the ability to synthesize a product with a molecular weight of more than $10^5$.

Moreover, it has also been discovered that, when the trans-prenyltransferase, which has activity and the ability to synthesize a product with a molecular weight of about $10^3$ when not bound to any lipid membrane, is fused to a membrane-binding peptide, it can still synthesize a product with a molecular weight of about $10^3$ even in the presence of a lipid membrane.

From these results, it has been found that for a trans-prenyltransferase having the ability to synthesize a product with a molecular weight of $10^4$ or more when not bound to any lipid membrane, it is possible to produce a product with a higher molecular weight by binding the trans-prenyltransferase to a lipid membrane so that the product is accumulated in the membrane. Accordingly, the present disclosure has been completed.

Specifically, the present disclosure relates to a method for producing a trans-polyisoprenoid, the method including binding to a lipid membrane in vitro a trans-prenyltransferase (tPT) family protein capable of producing a product with a molecular weight of $10^4$ or more when not bound to any lipid membrane.

Advantageous Effects of Disclosure

The method for producing a trans-polyisoprenoid according to the present disclosure includes binding to a lipid membrane in vitro a trans-prenyltransferase (tPT) family protein capable of producing a product with a molecular weight of $10^4$ or more when not bound to any lipid membrane. The binding of the tPT family protein to a lipid membrane enables the synthesis of a trans-polyisoprenoid having a molecular weight of more than $10^5$ in the lipid membrane. Thus, it is possible to provide a method for producing a trans-polyisoprenoid with a molecular weight of more than $10^5$ in an enzymatic manner.

The method for producing a pneumatic tire of the present disclosure includes kneading a trans-polyisoprenoid obtained by the method for producing a trans-polyisoprenoid with an additive to obtain a kneaded mixture; forming a green tire from the kneaded mixture; and vulcanizing the green tire. This method uses a trans-polyisoprenoid with a molecular weight of more than $10^5$ to produce a pneumatic tire. Thus, it is possible to produce a pneumatic tire using a trans-polyisoprenoid with a molecular weight of more than $10^5$.

The method for producing a rubber product of the present disclosure includes kneading a trans-polyisoprenoid obtained by the method for producing a trans-polyisoprenoid with an additive to obtain a kneaded mixture; forming a raw rubber product from the kneaded mixture; and vulcanizing the raw rubber product. This method uses a trans-polyisoprenoid with a molecular weight of more than $10^5$ to produce a rubber product. Thus, it is possible to produce a rubber product using a trans-polyisoprenoid with a molecular weight of more than $10^5$.

The vector of the present disclosure contains a gene coding for a trans-prenyltransferase (tPT) family protein capable of producing a product with a molecular weight of $10^4$ or more when not bound to any lipid membrane. When the vector is introduced into an organism by gene recombination techniques, a trans-polyisoprenoid with a molecular weight of more than $10^5$ can be produced in an enzymatic manner in the organism. Thus, the transgenic organism into which the vector has been introduced can produce a trans-polyisoprenoid with a molecular weight of more than $10^5$ in an enzymatic manner.

The method for producing a pneumatic tire of the present disclosure includes kneading a trans-polyisoprenoid obtained from the transgenic organism with an additive to obtain a kneaded mixture; forming a green tire from the kneaded mixture; and vulcanizing the green tire. This method uses a trans-polyisoprenoid with a molecular weight of more than $10^5$ to produce a pneumatic tire. Thus, it is possible to produce a pneumatic tire using a trans-polyisoprenoid with a molecular weight of more than $10^5$.

The method for producing a rubber product of the present disclosure includes kneading a trans-polyisoprenoid obtained from the transgenic organism with an additive to obtain a kneaded mixture; forming a raw rubber product from the kneaded mixture; and vulcanizing the raw rubber product. This method uses a trans-polyisoprenoid with a molecular weight of more than $10^5$ to produce a rubber product. Thus, it is possible to produce a rubber product using a trans-polyisoprenoid with a molecular weight of more than $10^5$.

DESCRIPTION OF EMBODIMENTS

Figure 1:
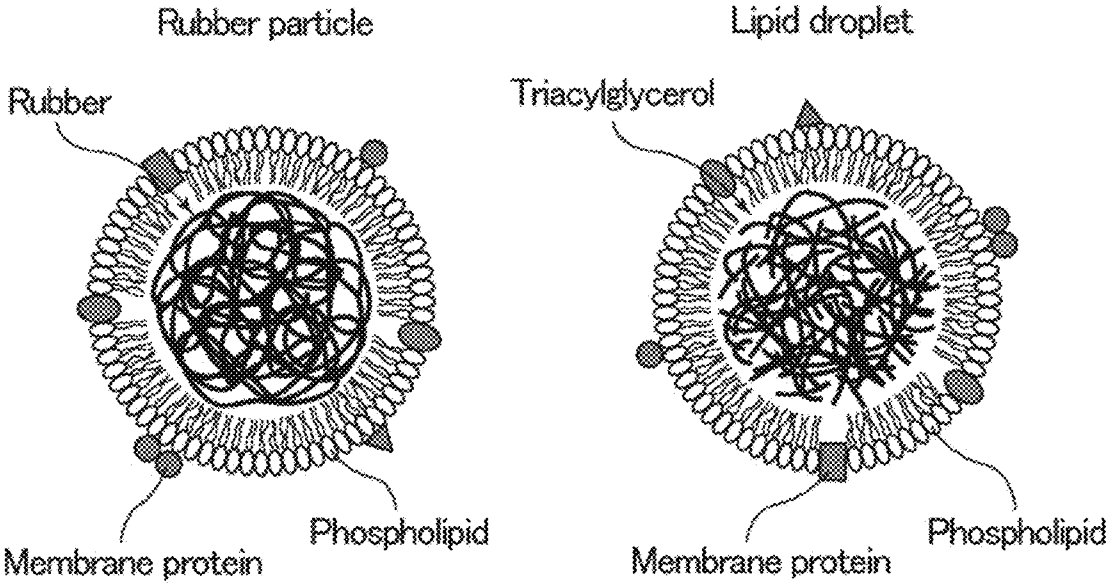
FIG. 1 shows schematic diagrams illustrating the structures of a rubber particle and a lipid droplet.

The method for producing a trans-polyisoprenoid of the present disclosure includes binding to a lipid membrane in vitro a trans-prenyltransferase (tPT) family protein capable of producing a product with a molecular weight of $10^4$ or more when not bound to any lipid membrane.

When a tPT family protein capable of producing a product with a molecular weight of $10^4$ or more when not bound to any lipid membrane is bound to a lipid membrane in vitro (for example, in a reaction vessel such as a test tube or a plant), a trans-polyisoprenoid with a molecular weight of more than $10^5$ can be synthesized (produced in an enzymatic manner) in the lipid membrane.

It should be noted that the production method of the present disclosure may include other steps as long as it includes the binding step. Moreover, the steps may each be performed once or may be repeated multiple times.

Moreover, the amount of the tPT family protein bound to a lipid membrane is not limited in the present disclosure.

According to the present disclosure, a trans-polyisoprenoid with a molecular weight of more than $10^5$ can be enzymatically produced in vitro, for example, by expressing a tPT family protein using a cell-free protein expression system in the presence of a lipid membrane and binding the tPT family protein to the lipid membrane.

Moreover, the vector of the present disclosure contains a gene coding for a trans-prenyltransferase (tPT) family protein capable of producing a product with a molecular weight of $10^4$ or more when not bound to any lipid membrane. Thus, when the vector is introduced into an organism by gene recombination techniques, a trans-polyisoprenoid with a molecular weight of more than $10^5$ can be produced in an enzymatic manner in the organism.

Since every organism has a lipid membrane, an organism can be transformed using the gene coding for the tPT family protein, whereby a trans-polyisoprenoid with a molecular weight of more than $10^5$ can be enzymatically produced in vivo.

Thus, according to the present disclosure, a trans-polyisoprenoid (trans-1,4-polyisoprene) with a molecular weight of more than $10^5$ can be produced in an enzymatic manner in vitro or in vivo.

In the present disclosure, a tPT family protein capable of producing a product with a molecular weight of $10^4$ or more when not bound to any lipid membrane may be bound to a lipid membrane so that the product can be accumulated in the lipid membrane, thereby increasing the molecular weight of the product. Thus, it is possible to synthesize (produce in an enzymatic manner) a trans-polyisoprenoid with a molecular weight of more than $10^5$, which is higher than that obtained when not bound to any lipid membrane.

Meanwhile, as described above, when a tPT family protein only capable of producing a product with a molecular weight of about $10^3$ when not bound to any lipid membrane is bound to a lipid membrane, it can still synthesize a product with a molecular weight of about $10^3$.

The difference between the two is not clear but it is assumed as follows.

The chain length of the product obtained by a prenyltransferase capable of synthesizing a product with a molecular weight of less than $10^4$ is controlled by the spatial size of the product elongation site. For example, for undecaprenyl diphosphate synthase (UPPS), the reaction stops when the product chain length reaches C55 undecaprenyl diphosphate (molecular weight: about 926) presumably because it hits the amino acid at the bottom of the space (cleft) of the product chain length. However, this mechanism for control of the molecular weight of the product is limited to when the product has a chain length shorter than that of the enzyme. Therefore, for an enzyme capable of producing a product with a molecular weight higher than that of the enzyme, such as trans-isoprene rubber, it is considered that there is no bottom to determine the product chain length, so that a product having a size larger than that of the enzyme can be synthesized by penetrating spatially.

Moreover, the chain length of the product not controlled by the enzyme structure is considered to be controlled by the reaction environment.

When the product chain length is controlled reaction-environmentally, the solubility of the product is considered to be a factor in determining the chain length of the product. Specifically, when reacted in an aqueous solution without being bound to any lipid membrane, the product is exposed to the aqueous solution outside the enzyme as the elongation reaction of the product proceeds. Meanwhile, it is considered that the longer the product chain length, the lower the hydrophilicity, the lower the stability in the aqueous solution. Thus, the product elongation is considered to stop at a certain chain length.

The experimental results for a trans-polyisoprenoid suggested that the product might have a molecular weight of about $10^4$ when it stopped elongation in the aqueous solution. Thus, an enzyme having the ability to synthesize a product with a molecular weight of about $10^4$ in an aqueous solution is considered to be a reaction-environmentally controlling enzyme. In contrast, an enzyme only capable of synthesizing a product of less than $10^4$ is considered to be an enzyme that controls the product chain length enzyme-structurally.

In the case of a reaction-environmentally controlling enzyme, the chain length of the product is expected be changed by altering the reaction environment. This time, it is considered that the molecular weight of the product was increased by the binding the enzyme to a lipid membrane to alter the reaction environment, while an enzyme-structurally controlling enzyme synthesized a product with the same molecular weight enzyme-structurally, without depending on the reaction environment.

Herein, the molecular weight is determined by gel permeation chromatography (GPC), specifically by the method described in EXAMPLES.

Herein, the phrase "when not bound to any lipid membrane" refers to a state in which no lipid membrane is present in the system, particularly a state in which the protein is not bound to any lipid membrane.

Also, herein, the term "tPT family protein capable of producing a product with a molecular weight of $10^4$ or more when not bound to any lipid membrane" refers to a tPT family protein that can produce a product with a molecular weight of $10^4$ or more, for example, when the tPT family protein is expressed in *Escherichia coli*, i.e., when not bound to any lipid membrane, and then an enzymatic reaction of the tPT family protein is performed, more specifically under conditions where the tPT family protein is not bound to any lipid membrane.

Herein, the expression "a tPT family protein is bound to a lipid membrane" means that, for example, the tPT family protein is fully or partially incorporated into the lipid membrane or inserted into the membrane structure of the lipid membrane. It is not limited to these embodiments and also means embodiments in which, for example, the tPT family protein is localized on the surface or inside of the lipid membrane. Moreover, the concept of binding to a lipid membrane also includes embodiments in which the tPT family protein forms a complex with another protein bound to the lipid membrane to exist in the form of the complex on the lipid membrane.

Herein, the term "membrane-binding domain (also referred to as membrane-binding peptide domain, membrane-binding peptide)" refers to a hydrophobic amino acid sequence required for binding to a membrane transport signal sequence or a membrane, and conceptually encompasses a transmembrane domain (also referred to as transmembrane peptide domain, transmembrane peptide). Herein, the term "transmembrane domain" refers to a domain including a large number of highly hydrophobic amino acids for membrane penetration, such as a domain forming an α-helix structure in which hydrophobic amino acids for penetrating a lipid membrane are located outside.

Also, herein, the term "solubilization" means a state of being stably present in an aqueous solution without being precipitated by centrifugation or the like. For example, a membrane protein insoluble in water can be solubilized by deleting the membrane-binding domain from the membrane protein.

Figure 2:
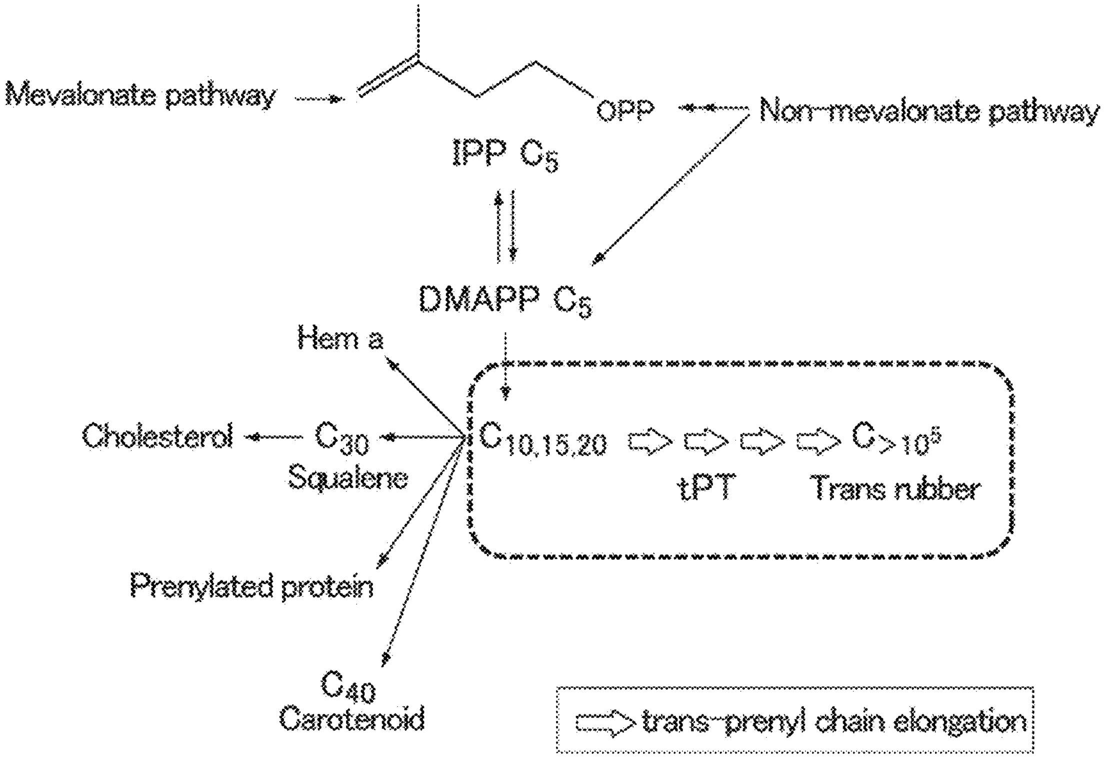
FIG. 2 is a schematic diagram illustrating part of a trans-polyisoprenoid biosynthesis pathway.

Also, herein, the term "trans-prenyltransferase (tPT) family protein" refers to an enzyme that catalyzes a reaction of trans-chain elongation of an isoprenoid compound. Specifically, for example, in plants, trans-polyisoprenoids are biosynthesized via trans-polyisoprenoid biosynthesis pathways as shown in FIG. 2, in which tPT family proteins are considered to be enzymes that catalyze the reactions enclosed by the dotted frame in FIG. 2. The tPT family proteins are characterized by having an amino acid sequence contained in the trans-IPPS HT domain (NCBI Accession No. cd00685).

Herein, the term "trans-polyisoprenoid" is a generic term for a polymer having isoprene units ($C_5H_8$) linked in a trans configuration (in particular, the percentage of trans-linkages based on the total linkages is preferably 90% or higher, more preferably 95% or higher, still more preferably 97% or higher.). Examples of the trans-polyisoprenoid include polymers such as trans-sesterterpene ($C_{25}$), trans-triterpene ($C_{30}$), trans-tetraterpene ($C_{40}$), trans-1,4-polyisoprene, and other trans rubbers. Also, herein, the term "isoprenoid" refers to a compound containing an isoprene unit ($C_5H_8$) and conceptually includes a polyisoprenoid.

(Method for Producing Trans-Polyisoprenoid)

The present disclosure relates to a method for producing a trans-polyisoprenoid, which includes binding to a lipid membrane in vitro a trans-prenyltransferase (tPT) family protein capable of producing a product with a molecular weight of $10^4$ or more when not bound to any lipid membrane.

(Lipid Membrane)

Non-limiting examples of the lipid membrane include lipid droplets (oil bodies), rubber particles, liposomes, nanodiscs, organelles, and endoplasmic reticula (microsomes). Moreover, the lipid membrane may be a lipid monolayer or a lipid bilayer, preferably a lipid monolayer. These may be used alone or in combinations of two or more. Moreover, the lipid membrane used may be either a lipid membrane derived from a natural product or an artificially synthesized lipid membrane. Lipid droplets, rubber particles, nanodiscs, and endoplasmic reticula (microsomes) are preferred among these, with lipid droplets or endoplasmic reticula (microsomes) being more preferred.

Herein, the term "lipid droplets" refers to inclusion bodies or cell organelles which have a membrane structure formed from phospholipids and membrane proteins (for example, oleosins or lipid droplet-associated protein (LDAP)/small rubber particle protein (SRPP) family proteins) and store triacylglycerols therein, as shown in FIG. 1. They exist in both prokaryotes and eukaryotes, including all plants.

Lipid droplets are also called oil droplets, fat droplets, oil bodies, or LD.

The lipid droplets may be of any origin and may be derived from microorganisms (including algae and microalgae), animals, or plants.

Non-limiting examples of the plants include plants of the genus *Hevea* such as *Hevea brasiliensis*; plants of the genus *Sonchus* such as *Sonchus oleraceus, Sonchus asper*, and *Sonchus brachyotus*; plants of the genus *Solidago* such as *Solidago altissima, Solidago virgaurea* subsp. *asiatica, Solidago virgaurea* subsp. *leipcarpa, Solidago virgaurea* subsp. *leipcarpa* f. *paludosa, Solidago virgaurea* subsp. *gigantea*, and *Solidago gigantea* Ait. var. *leiophylla* Fernald; plants of the genus *Helianthus* such as *Helianthus annuus, Helianthus argophyllus, Helianthus atrorubens, Helianthus debilis, Helianthus decapetalus*, and *Helianthus giganteus*; plants of the genus *Taraxacum* such as dandelion (*Taraxacum*), *Taraxacum venustum* H. Koidz, *Taraxacum hondoense* Nakai, *Taraxacum platycarpum* Dahlst, *Taraxacum japonicum, Taraxacum officinale* Weber, *Taraxacum koksaghyz*, and *Taraxacum brevicorniculatum*; plants of the genus *Ficus* such as *Ficus carica, Ficus elastica, Ficus pumila* L., *Ficus erecta* Thumb., *Ficus ampelas* Burm. f., *Ficus benguetensis* Merr., *Ficus irisana* Elm., *Ficus microcarpa* L. f., *Ficus septica* Burm. f., and *Ficus benghalensis*; plants of the genus *Parthenium* such as *Parthenium argentatum, Parthenium hysterophorus*, and annual ragweed (*Ambrosia artemisiifolia, Parthenium hysterophorus*); lettuce (*Lactuca sativa*), *Ficus benghalensis*, and other rubber-producing plants. Examples of plants other than rubber-producing plants include *Arabidopsis thaliana*, plants of the genus *Persea* such as *Persea americana*, plants of the genus *Sesamum* such as *Sesamum indicum*, plants of the genus *Brassica* such as *Brassica napus*, and plants of the genus *Camellia* such as *Camellia japonica*.

The microorganisms may be either prokaryotes or eukaryotes. Examples include prokaryotes such as microorganisms of the genera *Bacillus, Synechocystis*, and *Synechococcus*; and eukaryotic microorganisms such as yeasts and filamentous fungi.

Among the algae and microalgae, algae of the genus *Chlamydomonas, Chlorella, Phaeodactylum*, or *Nannochloropsis* are preferred because their genetic recombination techniques have been established. More preferred are algae of the genus *Chlamydomonas*.

The lipid droplets are preferably derived from plants, more preferably at least one selected from the group consisting of plants of the genera *Persea, Sesamum, Brassica*, and *Camellia*, still more preferably plants of the genus *Persea*, particularly preferably *Persea americana*.

The lipid droplets are also preferably derived from microorganisms, more preferably algae or microalgae, still more preferably algae of the genus *Chlamydomonas, Chlorella, Phaeodactylum*, or *Nannochloropsis*, particularly preferably algae of the genus *Chlamydomonas*.

The lipid droplets may be prepared by any method, including known methods. For example, a plant piece may be crushed in a buffer, followed by filtration and centrifugation to collect fat pads. The fat pads may also be washed, if necessary. Then, centrifugation may be performed to separate lipid droplets from the fat pads.

The centrifugation may be carried out, for example, at 15,000 to 20,000×g for 15 to 60 minutes.

Moreover, the centrifugation temperature is preferably 0° C. to 10° C., more preferably 2° C. to 8° C., particularly preferably 4° C.

Lipid droplets derived from *Persea americana* can be prepared according to the method described in WO2021/010101, for example.

Herein, the term "endoplasmic reticula (microsomes)" refers to endomembrane systems having a filamentous or network structure found in cells, and encompasses membrane vesicles that are torn off from the endoplasmic reticula when the cells are disrupted.

The endoplasmic reticula (microsomes) may be of any origin and may be derived from microorganisms, animals, or plants.

The endoplasmic reticula (microsomes) may be prepared by any method, including known methods. Exemplary methods include disrupting cells by ultrasonication or French press, followed by recovery and preparation through centrifugation such as density gradient centrifugation.

The origin of the rubber particles is not limited. For example, the rubber particles may be derived from latex of rubber-producing plants such as *Hevea brasiliensis, Taraxacum kok-saghyz, Parthenium argentatum, Sonchus oleraceus*, or *Ficus elastica*.

The particle size of the rubber particles is also not limited. Rubber particles having a predetermined particle size may be sorted out and used, or a mixture of rubber particles having different particle sizes may be used. Even when rubber particles having a predetermined particle size are sorted out and used, the rubber particles used may be either small rubber particles (SRP) having a small particle size or large rubber particles (LRP) having a large particle size.

Commonly used methods may be employed for sorting out the rubber particles having a predetermined particle size, including, for example, methods which involve centrifugation, preferably multistage centrifugation. A specific method includes centrifugation at 500-1500×g, centrifugation at 1700-2500×g, centrifugation at 7000-9000×g, centrifugation at 15000-25000×g, and centrifugation at 40000-60000×g, carried out in that order. Here, the duration of each centrifugation treatment is preferably at least 20 minutes, more preferably at least 30 minutes, still more preferably at least 40 minutes, but is preferably 120 minutes or less, more preferably 90 minutes or less. Moreover, the temperature for each centrifugation treatment is preferably 0° C. to 10° C., more preferably 2° C. to 8° C., particularly preferably 4° C.

(Trans-Prenyltransferase (tPT) Family Protein Capable of Producing a Product with a Molecular Weight of $10^4$ or More when not Bound to any Lipid Membrane)

Next, a trans-prenyltransferase (tPT) family protein capable of producing a product with a molecular weight of $10^4$ or more when not bound to any lipid membrane is described.

The trans-prenyltransferase (tPT) family protein capable of producing a product with a molecular weight of $10^4$ or more when not bound to any lipid membrane may be any tPT family protein capable of producing a product with a molecular weight of $10^4$ or more when not bound to any lipid membrane.

An embodiment of a tPT family protein capable of producing a product with a molecular weight of $10^4$ or more when not bound to any lipid membrane is a protein which has a membrane-binding domain and which can produce a product with a molecular weight of $10^4$ or more in an aqueous layer when not bound to any lipid membrane after solubilization.

A protein with a membrane-binding domain (membrane protein) cannot usually be solubilized in an aqueous layer. However, it can be solubilized by deleting the membrane-binding domain from the membrane protein. Moreover, it is sufficient that the protein after solubilization is capable of producing a product with a molecular weight of $10^4$ or more in an aqueous layer when not bound to any lipid membrane.

Another embodiment of a tPT family protein capable of producing a product with a molecular weight of $10^4$ or more when not bound to any lipid membrane is a protein to which the ability to bind to a lipid membrane has been imparted by fusing a membrane-binding peptide to a protein having no membrane-binding domain and capable of producing a product with a molecular weight of $10^4$ or more in an aqueous layer when not bound to any lipid membrane.

When a protein having no membrane-binding domain is capable of producing a product with a molecular weight of $10^4$ or more in an aqueous layer when not bound to any lipid membrane, fusing a membrane-binding peptide to the "protein having no membrane-binding domain and capable of producing a product with a molecular weight of $10^4$ or more in an aqueous layer when not bound to any lipid membrane" can impart the ability to bind to a lipid membrane to the protein having no membrane-binding domain which has no ability to bind to a lipid membrane.

As described above, the present disclosure features the use of a trans-prenyltransferase (tPT) family protein capable of producing a product with a molecular weight of $10^4$ or more when not bound to any lipid membrane. The tPT family protein is desirably a protein which originally contains a membrane-binding peptide but may be a protein which does not originally contain a membrane-binding peptide and has been fused to a membrane-binding peptide by genetic engineering. Specifically, the tPT family protein may be any protein that is capable of producing a product with a molecular weight of $10^4$ or more when not bound to any lipid membrane and also has the innate or acquired ability to bind to a lipid membrane.

The origin of the tPT family protein capable of producing a product with a molecular weight of $10^4$ or more when not bound to any lipid membrane or the protein having no membrane-binding domain and capable of producing a product with a molecular weight of $10^4$ or more in an aqueous layer when not bound to any lipid membrane is not limited. Preferably, the protein is derived from a trans rubber-producing plant.

Non-limiting examples of the trans rubber-producing plant include plants of the genus *Manilkara* such as *Manilkara zapota* and plants of the genus *Eucommia* such as *Eucommia ulmoides*. Plants of the genus *Manilkara* are preferred among these, with *Manilkara zapota* being more preferred.

A specific example of the trans-prenyltransferase (tPT) family protein capable of producing a product with a molecular weight of $10^4$ or more when not bound to any lipid membrane is the following protein [1]:

[1] a protein having the amino acid sequence represented by SEQ ID NO:4 (the amino acid sequence of tPT2 derived from *Manilkara zapota*)

It is also known that proteins having one or more amino acid substitutions, deletions, insertions, or additions relative to the original amino acid sequence can still have the inherent function. Thus, another specific example of the tPT family protein is the following protein [2]:

[2] a protein having an amino acid sequence containing one or more amino acid substitutions, deletions, insertions, and/or additions relative to the amino acid sequence represented by SEQ ID NO:4, and capable of catalyzing a reaction of trans-chain elongation of an isoprenoid compound to produce a product with a molecular weight of $10^4$ or more when not bound to any lipid membrane.

Here, in order to maintain the function of the tPT family protein, the protein preferably has an amino acid sequence containing one or more, more preferably 1 to 95, still more preferably 1 to 71, further preferably 1 to 47, particularly preferably 1 to 24, most preferably 1 to 9, even most preferably 1 to 5 amino acid substitutions, deletions, insertions, and/or additions relative to the amino acid sequence represented by SEQ ID NO:4.

Among other amino acid substitutions, conservative substitutions are preferred. Specific examples include substitutions within each of the following groups in the parentheses: (glycine, alanine), (valine, isoleucine, leucine), (aspartic acid, glutamic acid), (asparagine, glutamine), (serine, threonine), (lysine, arginine), and (phenylalanine, tyrosine).

It is also known that proteins with amino acid sequences having high sequence identity to the original amino acid sequence can also have similar functions. Thus, another specific example of the tPT family protein is the following protein [3]:

[3] a protein having an amino acid sequence with at least 80% sequence identity to the amino acid sequence represented by SEQ ID NO:4, and capable of catalyzing a reaction of trans-chain elongation of an isoprenoid compound to produce a product with a molecular weight of $10^4$ or more when not bound to any lipid membrane.

Here, in order to maintain the function of the tPT family protein, the sequence identity to the amino acid sequence represented by SEQ ID NO:4 is preferably at least 85%, more preferably at least 90%, still more preferably at least 95%, particularly preferably at least 98%, most preferably at least 99%.

Herein, the sequence identity between amino acid sequences or nucleotide sequences may be determined using the algorithm BLAST [Pro. Natl. Acad. Sci. USA, 90, 5873 (1993)] developed by Karlin and Altschul or FASTA [Methods Enzymol., 183, 63 (1990)].

Whether it is a protein having the above enzyme activity may be determined by, for example, conventional techniques, such as by expressing a target protein in a transformant produced by introducing a gene coding for the target protein into *Escherichia coli* or other host organism, and determining whether or not it is capable of catalyzing a reaction of trans-chain elongation of an isoprenoid compound to produce a product with a molecular weight of $10^4$ or more when not bound to any lipid membrane.

Genes coding for tPT family proteins as described above are possessed by rubber-producing plants, as well as other organisms such as plants other than rubber-producing plants, animals, and microorganisms. Of course, the tPT family proteins from the latter organisms are naturally not involved in rubber synthesis. In spite of this, according to the present disclosure, trans rubber can be synthesized in a lipid membrane by binding any tPT family protein to the lipid membrane, regardless of the origin, type, etc. of the protein. Thus, according to the present disclosure, trans rubber can be synthesized in a lipid membrane by using any tPT family protein, regardless of, for example, whether the gene coding for the tPT family protein is derived from a rubber-producing plant or any other organism, or whether it is naturally involved in rubber synthesis. This is strongly suggested by the mechanism already suggested in PCT/JP2016/069172 by the present inventors (the mechanism which shows that the host to be transfected, or in other words the environment in which the cis-prenyltransferase (CPT) family protein is expressed is more important for rubber synthesis activity than the origin or type of the CPT family protein).

The tPT family protein used in the present disclosure desirably has a transmembrane domain on the N-terminal side to have a higher affinity for a lipid membrane. In the case of a wild type having no transmembrane domain, a transmembrane domain may be artificially fused to the N-terminal side of the tPT family protein. Although the amino acid sequence of the transmembrane domain to be fused is not limited, it is desirably the amino acid sequence of a transmembrane domain carried by a protein that is inherently bound to a lipid membrane in nature.

The gene coding for the tPT family protein may be any gene that codes for the tPT family protein to express and produce the tPT family protein capable of producing a product with a molecular weight of $10^4$ or more when not bound to any lipid membrane. Specific examples of the gene include the following DNAs [1] and [2]:

[1] a DNA having the nucleotide sequence represented by SEQ ID NO:3; and

[2] a DNA which hybridizes under stringent conditions to a DNA having a nucleotide sequence complementary to the nucleotide sequence represented by SEQ ID NO:3, and which codes for a protein capable of catalyzing a reaction of trans-chain elongation of an isoprenoid compound to produce a product with a molecular weight of $10^4$ or more when not bound to any lipid membrane.

Herein, the term "hybridize" means a process in which a DNA hybridizes to a DNA having a specific nucleotide sequence or a part of the DNA. Thus, the DNA having a specific nucleotide sequence or part of the DNA may have a nucleotide sequence long enough to be usable as a probe in Northern or Southern blot analysis or as an oligonucleotide primer in polymerase chain reaction (PCR) analysis. The DNA to be used as a probe may have a length of at least 100 bases, preferably at least 200 bases, more preferably at least 500 bases although it may be a DNA of at least 10 bases, preferably at least 15 bases.

Techniques to perform DNA hybridization experiments are well known. The hybridization conditions under which experiments are performed may be determined in accordance with, for example, Molecular Cloning, 2nd ed. and 3rd ed. (2001), Methods for General and Molecular Bacteriology, ASM Press (1994), Immunology methods manual, Academic press (Molecular), and many other standard textbooks.

The stringent conditions may include, for example, overnight incubation at 42° C. of a DNA-immobilized filter and a DNA probe in a solution containing 50% formamide, 5×SSC (750 mM sodium chloride, 75 mM sodium citrate), 50 mM sodium phosphate (pH 7.6), 5×Denhardt's solution, 10% dextran sulfate, and 20 μg/L denatured salmon sperm DNA, followed by washing the filter for example in a 0.2×SSC solution at approximately 65° C. Less stringent conditions may also be used. Changes in stringency may be accomplished through the manipulation of the formamide concentration (lower percentages of formamide result in lower stringency), salt concentrations, or temperature. For example, low stringent conditions include overnight incubation at 37° C. in a solution containing 6×SSCE (20×SSCE: 3 mol/L sodium chloride, 0.2 mol/L sodium dihydrogen phosphate, 0.02 mol/L EDTA, pH 7.4), 0.5% SDS, 30% formamide, and 100 μg/L denatured salmon sperm DNA, followed by washing in a 1×SSC solution containing 0.1% SDS at 50° C. In addition, to achieve even lower stringency, washes performed following hybridization may be done at higher salt concentrations (e.g., 5×SSC) in the above-mentioned low stringent conditions.

Variations in the above conditions may be accomplished through the inclusion or substitution of blocking reagents used to suppress background in hybridization experiments. The inclusion of blocking reagents may require modification of the hybridization conditions for compatibility.

The DNA capable of hybridization under stringent conditions as described above may have a nucleotide sequence with at least 80%, preferably at least 90%, more preferably at least 95%, still more preferably at least 98%, particularly preferably at least 99% sequence identity to the nucleotide sequence represented by SEQ ID NO:3 as calculated using a program such as BLAST or FASTA with the parameters mentioned above.

Whether the DNA which hybridizes to the aforementioned DNA under stringent conditions is a DNA coding for a protein having a predetermined enzyme activity may be determined by conventional techniques, such as by expressing a target protein in a transformant produced by introducing a gene coding for the target protein into *Escherichia coli* or other host organism, and determining the presence or absence of the function of the target protein by the corresponding activity measuring method.

Moreover, conventional techniques may be employed to identify the amino acid sequence or nucleotide sequence of the protein. For example, total RNA is extracted from a growing plant, the mRNA is optionally purified, and a cDNA is synthesized by a reverse transcription reaction. Subsequently, degenerate primers are designed based on the amino acid sequence of a known protein corresponding to the target protein, a DNA fragment is partially amplified by RT-PCR, and the sequence is partially identified. Then, the full-length nucleotide sequence or amino acid sequence is identified, e.g. by the RACE method. The RACE method (rapid amplification of cDNA ends method) refers to a method in which, when the nucleotide sequence of a cDNA is partially known, PCR is performed based on the nucleotide sequence data of such a known region to clone the unknown region extending to the cDNA terminal. This method can clone full-length cDNA by PCR without preparing a cDNA library.

Here, the degenerate primers may each preferably be prepared from a plant-derived sequence having a highly similar sequence part to the target protein.

Moreover, if the nucleotide sequence coding for the protein is known, the full-length nucleotide sequence or amino acid sequence can be identified by designing a primer containing a start codon and a primer containing a stop codon using the known nucleotide sequence, followed by performing RT-PCR using a synthesized cDNA as a template.

(Membrane-Binding Peptide)

As described above, when a protein having no membrane-binding domain is capable of producing a product with a molecular weight of $10^4$ or more in an aqueous layer when not bound to any lipid membrane, fusing a membrane-binding peptide to the "protein having no membrane-binding domain and capable of producing a product with a molecular weight of $10^4$ or more in an aqueous layer when not bound to any lipid membrane" can impart the ability to bind to a lipid membrane to the protein having no membrane-binding domain which has no ability to bind to a lipid membrane.

The origin of the membrane-binding peptide is as described for the origin of the lipid membrane, including its preferred embodiments. The membrane-binding peptide is preferably derived from a plant, more preferably at least one selected from the group consisting of plants of the genera *Persea, Sesamum, Brassica*, and *Camellia*, still more preferably a plant of the genus *Persea*, particularly preferably *Persea americana.*

The membrane-binding peptide is also preferably derived from a microorganism, more preferably an alga or microalga, still more preferably an alga of the genus *Chlamydomonas, Chlorella, Phaeodactylum*, or *Nannochloropsis*, particularly preferably an alga of the genus *Chlamydomonas.*

Moreover the lipid membrane and membrane-binding peptide used are preferably of the same origin. Then, the protein fused to the membrane-binding peptide will suitably have the ability to bind to the lipid membrane.

The membrane-binding peptide may be any peptide that can impart the ability to bind to a lipid membrane and is preferably a peptide derived from a protein capable of binding to a lipid membrane, more preferably a peptide derived from a class II protein capable of binding to a lipid membrane. Here, it is sufficient that the peptide derived from a protein capable of binding to a lipid membrane has the ability to bind to a lipid membrane. Thus, the whole or a part of the peptide from a protein capable of binding to a lipid membrane is usable. Although the peptide capable of binding to a lipid membrane is not limited, it is desirably a peptide from a transmembrane domain carried by a protein that is inherently bound to a lipid membrane in nature.

Here, class II proteins refers to lipid droplet-binding proteins characterized by being capable of binding to lipid droplets and further by localizing to the cytosol when lipid droplets are absent in the cells (c.f., Gidda et al., Plant Physiology, April 2016, Vol. 170, pp. 2052-2071). Unlike class I proteins which localize to ER fractions when lipid droplets are absent, class II proteins can transfer between the cytosol and lipid droplets.

Non-limiting examples of proteins capable of binding to lipid droplets which are class II proteins include lipid droplet-associated protein (LDAP)/small rubber particle protein (SRPP) family proteins. Preferred are lipid droplet-associated protein (LDAP)/small rubber particle protein (SRPP) family proteins, among others.

Other examples of the membrane-binding peptide include a membrane-binding domain derived from major lipid droplet protein (MLDP).

A specific example of the gene coding for the membrane-binding domain derived from MLDP is the following DNA [1] or [2]:

[1] a DNA having the nucleotide sequence represented by SEQ ID NO:5 (the nucleotide sequence of MLDP derived from *Chlamydomonas*); or

[2] a DNA which hybridizes under stringent conditions to a DNA having a nucleotide sequence complementary to the nucleotide sequence represented by SEQ ID NO:5, and which codes for a protein having the ability to bind to a lipid membrane.

Herein, the term "hybridize" means a process in which a DNA hybridizes to a DNA having a specific nucleotide sequence or a part of the DNA. Thus, the DNA having a specific nucleotide sequence or part of the DNA may have a nucleotide sequence long enough to be usable as a probe in Northern or Southern blot analysis or as an oligonucleotide primer in polymerase chain reaction (PCR) analysis. The DNA to be used as a probe may have a length of at least 100 bases, preferably at least 200 bases, more preferably at least 500 bases although it may be a DNA of at least 10 bases, preferably at least 15 bases.

Techniques to perform DNA hybridization experiments are well known. The hybridization conditions under which experiments are performed may be determined in accordance with, for example, Molecular Cloning, 2nd ed. and 3rd ed. (2001), Methods for General and Molecular Bacteriology, ASM Press (1994), Immunology methods manual, Academic press (Molecular), and many other standard textbooks.

The stringent conditions may include, for example, overnight incubation at 42° C. of a DNA-immobilized filter and a DNA probe in a solution containing 50% formamide, 5×SSC (750 mM sodium chloride, 75 mM sodium citrate), 50 mM sodium phosphate (pH 7.6), 5×Denhardt's solution, 10% dextran sulfate, and 20 μg/L denatured salmon sperm DNA, followed by washing the filter for example in a 0.2×SSC solution at approximately 65° C. Less stringent conditions may also be used. Changes in stringency may be accomplished through the manipulation of formamide concentration (lower percentages of formamide result in lower stringency), salt concentrations or temperature. For example, low stringent conditions include overnight incubation at 37° C. in a solution containing 6×SSCE (20×SSCE: 3 mol/L sodium chloride, 0.2 mol/L sodium dihydrogen phosphate, 0.02 mol/L EDTA, pH 7.4), 0.5% SDS, 30% formamide, and 100 μg/L denatured salmon sperm DNA, followed by washing in a 1×SSC solution containing 0.1% SDS at 50° C. In addition, to achieve even lower stringency, washes performed following hybridization may be done at higher salt concentrations (e.g., 5×SSC) in the above-mentioned low stringent conditions.

Variations in the above conditions may be accomplished through the inclusion or substitution of blocking reagents used to suppress background in hybridization experiments. The inclusion of blocking reagents may require modification of the hybridization conditions for compatibility.

The DNA capable of hybridization under stringent conditions as described above may have a nucleotide sequence with at least 80%, preferably at least 90%, more preferably at least 95%, still more preferably at least 98%, particularly preferably at least 99% sequence identity to the nucleotide sequence represented by SEQ ID NO:5 as calculated using a program such as BLAST or FASTA with the parameters mentioned above.

Whether the DNA which hybridizes to the aforementioned DNA under stringent conditions is a DNA coding for a protein having a predetermined function may be determined by conventional techniques, such as by expressing a target protein in a transformant produced by introducing a gene coding for the target protein into *Escherichia coli* or other host organism, and determining the presence or absence of the function of the target protein.

Moreover, the amino acid sequence or nucleotide sequence of the protein may be identified by conventional techniques.

(Binding Step)

In the binding step, as long as the trans-prenyltransferase (tPT) family protein capable of producing a product with a molecular weight of $10^4$ or more when not bound to any lipid membrane is bound to a lipid membrane in vitro, additional proteins may further be bound thereto.

Although the origin of the additional proteins is not limited, the additional proteins are preferably derived from any of the plants mentioned above, more preferably rubber-producing plants, still more preferably at least one selected from the group consisting of plants of the genera *Hevea, Sonchus, Taraxacum*, and *Parthenium*. In particular, they are further preferably derived from at least one species of plant selected from the group consisting of *Hevea brasiliensis, Sonchus oleraceus, Parthenium argentatum*, and *Taraxacum kok-saghyz*, particularly preferably *Hevea brasiliensis*.

The additional proteins may be any protein without any limitations, but from the standpoint of the rubber synthesis ability of the lipid membrane, they are each preferably a protein that originally exists on a lipid membrane in a rubber-producing plant. Here, the protein that exists on a lipid membrane may be a protein that binds to a large part of the membrane surface of a lipid membrane, or a protein that binds to the membrane of a lipid membrane so as to be inserted thereinto, or a protein that forms a complex with another protein bound to the membrane to exist on the membrane surface.

Examples of the protein that originally exists on a lipid membrane in a rubber-producing plant include Nogo-B receptor (NgBR), rubber elongation factor (REF), small rubber particle protein (SRPP), β-1,3-glucanase, and Hevein.

The binding step may be carried out using any means that can bind to a lipid membrane in vitro the tPT family protein capable of producing a product with a molecular weight of $10^4$ or more when not bound to any lipid membrane. An exemplary method includes performing protein synthesis in the presence of both a lipid membrane and a cell-free protein synthesis solution containing an mRNA coding for the tPT family protein to bind the tPT family protein to the lipid membrane.

The binding step preferably includes performing protein synthesis in the presence of both a lipid membrane and a cell-free protein synthesis solution containing an mRNA coding for the tPT family protein to bind the tPT family protein to the lipid membrane, among other methods.

In other words, it is preferred to obtain a lipid membrane bound to the tPT family protein by performing protein synthesis in the presence of both a lipid membrane and a cell-free protein synthesis solution containing an mRNA coding for the tPT family protein (more specifically, using a mixture of a lipid membrane with a cell-free protein synthesis solution containing an mRNA coding for the tPT family protein).

The protein synthesis in the presence of both a lipid membrane and a cell-free protein synthesis solution containing an mRNA coding for the tPT family protein is namely the synthesis of the tPT family protein by cell-free protein synthesis, and the synthesized tPT family protein maintains its biological function (native state). As the cell-free protein synthesis is performed in the presence of a lipid membrane, the synthesized tPT family protein in its native state can be bound to the lipid membrane.

Here, "performing protein synthesis in the presence of both a lipid membrane and the cell-free protein synthesis solution to bind the tPT family protein to the lipid membrane" means that, for example, each tPT family protein synthesized by the protein synthesis is fully or partially incorporated into the lipid membrane or inserted into the membrane structure of the lipid membrane. It is not limited to these embodiments and also means, for example, embodiments in which the protein is localized on the surface or inside of the lipid membrane. Moreover, the concept of binding to a lipid membrane also includes embodiments in which the protein forms a complex with another protein bound to the lipid membrane as described above to exist in the form of the complex on the lipid membrane.

Each mRNA coding for the tPT family protein serves as a translation template that can be translated to synthesize the tPT family protein.

A person skilled in the art can appropriately perform the binding step. For example, it can be performed as described in WO 2021/010101, WO 2018/116726, or by other methods.

The binding step preferably includes performing protein synthesis in the presence of both a lipid membrane and a cell-free protein synthesis solution containing an mRNA coding for the tPT family protein. Specifically, this can be accomplished by adding a lipid membrane to the cell-free protein synthesis solution at a suitable point either before or after the protein synthesis, preferably before the protein synthesis.

Moreover, the concentration of the lipid membrane to be present with the cell-free protein synthesis solution is preferably 5 to 50 g/L. In other words, 5 to 50 g of the lipid membrane is preferably present with 1 L of the cell-free protein synthesis solution. If the concentration of the lipid membrane to be present with the cell-free protein synthesis solution is less than 5 g/L, a rubber layer may not be formed by separation treatment (e.g., ultracentrifugation) for collecting the lipid membrane bound to the synthesized tPT family protein. It may therefore be difficult to collect the lipid membrane bound to the synthesized tPT family protein. Moreover, if the concentration of the lipid membrane to be present with the cell-free protein synthesis solution exceeds 50 g/L, each lipid membrane may aggregate, so that the synthesized tPT family protein may fail to bind well to the lipid membrane. The concentration of the lipid membrane is more preferably 10 to 40 g/L, still more preferably 15 to 35 g/L, particularly preferably 15 to 30 g/L.

Moreover, in the protein synthesis in the presence of both a lipid membrane and the cell-free protein synthesis solution, the lipid membrane may be additionally added as appropriate as the reaction proceeds. The cell-free protein synthesis solution and the lipid membrane are preferably present together during the period when the cell-free protein synthesis system is active, such as 3 to 48 hours, preferably 3 to 30 hours, more preferably 3 to 24 hours after the addition of the lipid membrane to the cell-free protein synthesis solution.

Examples of reaction systems or apparatuses for protein synthesis that can be used in the cell-free protein synthesis include a batch method (Pratt, J. M. et al., Transcription and Translation, Hames, 179-209, B. D. & Higgins, S. J., eds, IRL Press, Oxford (1984)), a continuous cell-free protein synthesis system in which amino acids, energy sources, and other components are supplied continuously to the reaction system (Spirin, A. S. et al., Science, 242, 1162-1164 (1988)), a dialysis method (Kigawa et al., 21st Annual Meeting of the Molecular Biology Society of Japan, WID 6), and an overlay method (instruction manual of PROTEIOS™ wheat germ cell-free protein synthesis core kit, Toyobo Co., Ltd.). Other methods may include supplying template RNA, amino acids, energy sources, and other components, if necessary, to the protein synthesis reaction system, and discharging the synthesis product or decomposition product as required.

Of these, the dialysis method is preferred for the following reason. The overlay method has the advantage of easy operation, but unfortunately the lipid membrane will disperse in the reaction solution and is difficult to efficiently bind to the synthesized tPT family protein. In contrast, in the dialysis method, since the amino acids used as raw materials of the tPT family protein to be synthesized can pass through the dialysis membrane while the lipid membrane cannot pass therethrough, it is possible to prevent the lipid membrane from dispersing and thus to efficiently bind the synthesized tPT family protein to the lipid membrane.

Here, the dialysis method refers to a method in which protein synthesis is performed using an apparatus in which the reaction solution for protein synthesis used in the cell-free protein synthesis is used as an internal dialysis solution and is separated from an external dialysis solution by a dialysis membrane capable of mass transfer. Specifically, for example, the synthesis reaction solution excluding the translation template is optionally pre-incubated for an appropriate amount of time, to which is then added the translation template and the mixture is put in an appropriate dialysis container as the internal reaction solution. Examples of the dialysis container include containers with a dialysis membrane attached to the bottom (e.g., Dialysis Cup 12,000 available from Daiichi Kagaku) and dialysis tubes (e.g., 12,000 available from Sanko Junyaku Co., Ltd.). The dialysis membrane used may have a molecular weight cutoff of 10,000 daltons or more, preferably about 12,000 daltons.

The external dialysis solution used may be a buffer containing amino acids. Dialysis efficiency can be increased by replacing the external dialysis solution with a fresh one when the reaction speed declines. The reaction temperature and time may be selected appropriately according to the protein synthesis system used. For example, in the case of a system using a wheat-derived germ extract, the reaction may be carried out usually at 10° C. to 40° C., preferably 18° C. to 30° C., more preferably 20° C. to 26° C., for 10 minutes to 48 hours, preferably 10 minutes to 30 hours, more preferably 10 minutes to 24 hours.

Moreover, since the mRNA coding for the tPT family protein contained in the cell-free protein synthesis solution can be easily broken down, the mRNA may be additionally added as appropriate during the protein synthesis reaction to make the protein synthesis more efficient. Thus, in another suitable embodiment of the present disclosure, the mRNA coding for the tPT family protein is additionally added during the protein synthesis reaction.

Here, the addition time, the number of additions, the addition amount, and other conditions of the mRNA are not limited, and may be selected appropriately.

In the production method of the present disclosure, the binding step may optionally be followed by collecting the lipid membrane.

The lipid membrane collection step may be carried out by any method that can collect the lipid membrane. It may be carried out by conventional methods for collecting lipid membranes. Specific examples include methods using centrifugation. When the lipid membrane is collected by such a centrifugation method, the centrifugal force, centrifugation time, and centrifugation temperature may be selected appropriately so as to be able to collect the lipid membrane. For example, the centrifugal force during the centrifugation is preferably 15000×g or more, more preferably 20000×g or more, still more preferably 25000×g or more. However, since increasing the centrifugal force too much is not expected to produce a correspondingly high separation effect, the upper limit of the centrifugal force is preferably 50000×g or less, more preferably 45000×g or less. The centrifugation time is preferably at least 20 minutes, more preferably at least 30 minutes, still more preferably at least 40 minutes. However, since increasing the centrifugation time too much is not expected to produce a correspondingly high separation effect, the upper limit of the centrifugation time is preferably 120 minutes or less, more preferably 90 minutes or less.

Moreover, from the standpoint of maintaining the activity of the tPT family protein bound to the lipid membrane, the centrifugation temperature is preferably 0° C. to 10° C., more preferably 2° C. to 8° C., particularly preferably 4° C.

For example, when the cell-free protein synthesis is performed, the lipid membrane and the cell-free protein synthesis solution are separated into the upper and lower layers, respectively, by the centrifugation method. The cell-free protein synthesis solution as the lower layer may then be removed to collect the lipid membrane bound to the tPT family protein. The collected lipid membrane may be re-suspended in an appropriate buffer with a neutral pH for storage.

Here, the lipid membrane collected after the lipid membrane collection step can be used in the production of a trans-polyisoprenoid without the need for further special treatment.

Further, the trans-polyisoprenoid produced by the method for producing a trans-polyisoprenoid can be recovered by subjecting the lipid membrane to the solidification step described below.

The solidification step may be carried out by any solidification method, such as by adding the lipid membrane to a solvent that does not dissolve trans-polyisoprenoids (trans rubber), such as ethanol, methanol, or acetone, or by adding an acid to the lipid membrane. Rubber can be recovered as solids from the lipid membrane by the solidification step. The obtained rubber may be dried if necessary before use.

(Method for Producing Rubber Product)

The method for producing a rubber product of the present disclosure includes: kneading a trans-polyisoprenoid obtained by the method for producing a trans-polyisoprenoid of the present disclosure with an additive to obtain a kneaded mixture; forming a raw rubber product from the kneaded mixture; and vulcanizing the raw rubber product.

The rubber product is not limited as long as it is a rubber product that can be produced from rubber, preferably natural rubber, and examples include pneumatic tires, rubber rollers, rubber fenders, gloves, and medical rubber tubes.

When the rubber product is a pneumatic tire or, in other words, when the method for producing a rubber product of the present disclosure is the method for producing a pneumatic tire of the present disclosure, the raw rubber product forming step corresponds to forming a green tire from the kneaded mixture, and the vulcanization step corresponds to vulcanizing the green tire. Thus, the method for producing a pneumatic tire of the present disclosure includes: kneading a trans-polyisoprenoid obtained by the method for producing a trans-polyisoprenoid with an additive to obtain a kneaded mixture; forming a green tire from the kneaded mixture; and vulcanizing the green tire.

<Kneading Step>

In the kneading step, the trans-polyisoprenoid produced by the method for producing a trans-polyisoprenoid is kneaded with an additive to obtain a kneaded mixture.

Any additive may be used, including additives used in the production of rubber products. For example, in the case where the rubber product is a pneumatic tire, examples of the additive include rubber components other than the trans-polyisoprenoid, reinforcing fillers such as carbon black, silica, calcium carbonate, alumina, clay, and talc, silane coupling agents, zinc oxide, stearic acid, processing aids, various antioxidants, softeners such as oils, waxes, vulcanizing agents such as sulfur, and vulcanization accelerators.

In the kneading step, kneading may be carried out using an open roll mill, a Banbury mixer, an internal mixer, or other rubber kneading machines.

<Raw Rubber Product Forming Step (Green Tire Forming Step in the Case of Tire)>

In the raw rubber product forming step, a raw rubber product (green tire in the case of tire) is formed from the kneaded mixture obtained in the kneading step.

The raw rubber product may be formed by any method, including appropriate methods used to form raw rubber products. For example, in the case where the rubber product is a pneumatic tire, the kneaded mixture obtained in the kneading step may be extruded into the shape of a tire component and then formed and assembled with other tire components in a usual manner on a tire building machine to form a green tire (unvulcanized tire).

<Vulcanization Step>

In the vulcanization step, the raw rubber product obtained in the raw rubber product forming step is vulcanized to obtain a rubber product.

The raw rubber product may be vulcanized by any method, including appropriate methods used to vulcanize raw rubber products. For example, in the case where the rubber product is a pneumatic tire, the green tire (unvulcanized tire) obtained in the raw rubber product forming step may be vulcanized by heating and pressing in a vulcanizer to obtain a pneumatic tire.

(Vector)

The vector of the present disclosure contains a gene coding for a trans-prenyltransferase (tPT) family protein capable of producing a product with a molecular weight of $10^4$ or more when not bound to any lipid membrane. When such a vector is introduced into an organism for transformation, as the gene coding for the tPT family protein capable of producing a product with a molecular weight of $10^4$ or more when not bound to any lipid membrane, contained in the vector is expressed, a trans-polyisoprenoid with a molecular weight of more than $10^5$ can be produced in an enzymatic manner in the organism.

The vector of the present disclosure may be prepared by inserting a nucleotide sequence of a gene coding for the tPT family protein, preferably a nucleotide sequence of a promoter and a nucleotide sequence of a gene coding for the tPT family protein, into a vector commonly known as a transformation vector by conventional techniques.

Examples of vectors that can be used to prepare the vector of the present disclosure include pBI vectors, binary vectors such as pGA482, pGAH, and pBIG, intermediate plasmids such as pLGV23Neo, pNCAT, and pMON200, and pH35GS containing GATEWAY cassette.

Examples of promoters that can be used to prepare the vector of the present disclosure include promoters generally used in gene recombination-related fields, such as CaMV35 and NOS promoters.

As long as the vector of the present disclosure contains a nucleotide sequence of a gene coding for the tPT family protein, it may contain other nucleotide sequences. In addition to these nucleotide sequences, the vector usually contains vector-derived sequences as well as other sequences such as a restriction enzyme recognition sequence, a spacer sequence, a marker gene sequence, and a reporter gene sequence.

Moreover, the vector of the present disclosure may contain a nucleotide sequence of a gene coding for a coenzyme, if necessary.

Examples of the marker gene include drug-resistant genes such as a kanamycin-resistant gene, a hygromycin-resistant gene, and a bleomycin-resistant gene. Moreover, the reporter gene may be introduced to determine the expression site in a plant. Examples of the reporter gene include a luciferase gene, a β-glucuronidase (GUS) gene, a green fluorescent protein (GFP), and a red fluorescent protein (RFP)

(Transgenic Organism and Method for Producing Trans-Polyisoprenoid Using the Transgenic Organism)

For example, a transgenic organism (transgenic cell) transformed to express the tPT family protein can be obtained by introducing the vector of the present disclosure into a cell, such as a plant cell. In other words, a transgenic organism into which a gene coding for the tPT family protein has been introduced can be obtained. Then, as the tPT family protein is expressed in the transgenic organism, a trans-polyisoprenoid with a molecular weight of more than $10^5$ can be produced in an enzymatic manner. Then, the synthesized trans-polyisoprenoid is accumulated in the lipid membrane in the cell.

The host into which the gene coding for the tPT family protein is to be introduced may be any organism containing a lipid membrane. Examples include microorganisms (including algae and microalgae), plants, and animals. Among these, the host is preferably a microorganism or a plant, more preferably a microorganism, still more preferably a microalga.

In general, it is difficult to synthesize a trans-polyisoprenoid using an organism. However, the synthesis of a trans-polyisoprenoid can be facilitated when the gene coding for the tPT family protein is introduced into the host described above.

The microorganisms may be either prokaryotes or eukaryotes. Examples include prokaryotes such as microorganisms of the genera *Escherichia, Bacillus, Synechocystis*, and *Synechococcus*; and eukaryotic microorganisms such as yeasts and filamentous fungi. Preferred among these is *Escherichia coli, Bacillus subtilis, Rhodosporidium toruloides*, or *Mortierella* sp., with *Escherichia coli* being more preferred.

Among the algae and microalgae, algae of the genera *Chlamydomonas, Chlorella, Phaeodactylum*, or *Nannochloropsis* are preferred because their genetic recombination techniques have been established. More preferred are algae of the genus *Nannochloropsis*. Specific examples of the algae of the genus *Nannochloropsis* include *Nannochloropsis oculata, Nannochloropsis gaditana, Nannochloropsis salina, Nannochloropsis oceanica, Nannochloropsis atomus, Nannochloropsis maculata, Nannochloropsis granulata*, and *Nannochloropsis* sp. *Nannochloropsis oculata* or *Nannochloropsis* gaditana is preferred among these, with *Nannochloropsis oculata* being more preferred.

Among the plants, *Arabidopsis thaliana, Brassica napus, Brassica rapa, Cocos nucifera, Elaeis guineensis, Cuphea, Glycine max, Zea mays, Oryza sativa, Helianthus annuus, Cinnamomum camphora*, or Jatropha curcas is preferred, with *Arabidopsis thaliana* being more preferred.

A method for preparing the transgenic organism is briefly described below although the transgenic organism may be prepared by conventional techniques.

The vector of the present disclosure may be introduced into a plant (including plant cells, such as calluses, cultured cells, spheroplasts, and protoplasts) by any method that can introduce DNA into plant cells. Examples include methods using agrobacterium (JP S59-140885 A, JP S60-70080 A, WO94/00977), electroporation methods (JP S60-251887 A), and methods using particle guns (gene guns) (JP 2606856 B, JP 2517813 B).

In addition, the transgenic organism may be prepared by introducing the vector of the present disclosure into, for example, an organism (e.g., a microorganism, yeast, animal cell, or insect cell) or a part thereof, an organ, a tissue, a cultured cell, a spheroplast, or a protoplast, e.g., by any of the above-described DNA introduction methods.

The transgenic organism can be produced by the above or other methods. Here, the form of the transgenic organism is not limited as long as it includes a transformed cell. The transgenic organism may be a single cell or may be a tissue or transformant of combined cells. Here, the transgenic organism conceptually includes not only transgenic organisms produced by the above methods, but also all of their progeny or clones and even progeny organisms obtained by passaging them.

For example, once obtaining transgenic plant cells into which the vector of the present disclosure has been introduced, progeny or clones can be produced from the transgenic plant cells by sexual or asexual reproduction, tissue culture, cell culture, cell fusion, or other techniques. Moreover, the transgenic plant cells, or their progeny or clones may be used to obtain reproductive materials (e.g., seeds, fruits, cuttings, stem tubers, root tubers, shoots, adventitious buds, adventitious embryos, calluses, protoplasts), which may then be used to produce the transgenic plant on a large scale.

Techniques to regenerate plants (transgenic plants) from transgenic plant cells are known. For example, Doi et al. disclose techniques for eucalyptus (Japanese patent application No. H11-127025), Fujimura et al. disclose techniques for rice (Fujimura et al., (1995), Plant Tissue Culture Lett., vol. 2: p. 74-), Shillito et al. disclose techniques for corn (Shillito et al., (1989), Bio/Technology, vol. 7: p. 581-), Visser et al. disclose techniques for potato (Visser et al., (1989), Theor. Appl. Genet., vol. 78: p. 589-), and Akama et al. disclose techniques for *Arabidopsis thaliana* (Akama et al., (1992), Plant Cell Rep., vol. 12: p. 7-). A person skilled in the art can regenerate plants from transgenic plant cells according to these documents.

Whether a target protein gene is expressed in a regenerated plant may be determined by well-known techniques. For example, Western blot analysis may be used to assess the expression of a target protein.

Seeds can be obtained from the transgenic plant, for example, as follows. The transgenic plant may be rooted in an appropriate medium and transplanted to water-containing soil in a pot. It may be grown under proper cultivation conditions to finally produce seeds, which are then collected. Moreover, plants can be grown from seeds, for example, as follows: the seeds obtained from the transgenic plant as described above may be sown in water-containing soil and grown under proper cultivation conditions into plants.

In the present disclosure, when the vector of the present disclosure is introduced into a cell, such as a plant cell, as the gene coding for the tPT family protein in the vector is expressed, a trans-polyisoprenoid with a molecular weight of more than $10^5$ can be produced in an enzymatic manner in the cell. Specifically, a trans-polyisoprenoid with a molecular weight of more than $10^5$ can be produced by culturing a transgenic organism produced as described above, a callus obtained from such transgenic plant cells, cells redifferentiated from the callus, etc. in an appropriate medium, or by growing a transgenic plant redifferentiated from the transgenic plant cells, plants grown from seeds collected from the transgenic plant, etc. under proper cultivation conditions.

(Method for Producing Rubber Product)

The method for producing a rubber product of the present disclosure includes: kneading a trans-polyisoprenoid obtained from the transgenic organism with an additive to obtain a kneaded mixture; forming a raw rubber product from the kneaded mixture; and vulcanizing the raw rubber product.

The rubber product is as described above.

When the rubber product is a pneumatic tire or, in other words, when the method for producing a rubber product of the present disclosure is the method for producing a pneumatic tire of the present disclosure, the raw rubber product forming step corresponds to forming a green tire from the kneaded mixture, and the vulcanization step corresponds to vulcanizing the green tire. Thus, the method for producing a pneumatic tire of the present disclosure includes: kneading a trans-polyisoprenoid obtained from the transgenic organism with an additive to obtain a kneaded mixture; forming a green tire from the kneaded mixture; and vulcanizing the green tire.

<Kneading Step>

In the kneading step, the trans-polyisoprenoid obtained from the transgenic organism is kneaded with an additive to obtain a kneaded mixture.

The trans-polyisoprenoid obtained from the transgenic organism may be obtained by harvesting a lipid membrane from the transgenic organism, and subjecting the harvested lipid membrane to the solidification step described below.

Here, the lipid membrane may be harvested from the transgenic organism by any method, including usual methods. For example, the lipid membrane may be harvested by cutting a part of the transgenic cells, crushing the cut tissue, and extracting the crushed tissue with an organic solvent.

<Solidification>

The harvested lipid membrane is subjected to a solidification step. The solidification may be carried out by any method, such as by adding the lipid membrane to a solvent that does not dissolve trans-polyisoprenoids (trans rubber), such as ethanol, methanol, or acetone, or by adding an acid to the lipid membrane. Rubber can be recovered as solids from the lipid membrane by the solidification step. The obtained rubber may be dried if necessary before use.

Any additive may be used, including additives used in the production of rubber products. For example, in the case where the rubber product is a pneumatic tire, examples of the additive include rubber components other than the rubber obtained from the latex described above, reinforcing fillers such as carbon black, silica, calcium carbonate, alumina, clay, and talc, silane coupling agents, zinc oxide, stearic acid, processing aids, various antioxidants, softeners such as oils, waxes, vulcanizing agents such as sulfur, and vulcanization accelerators.

In the kneading step, kneading may be carried out using an open roll mill, a Banbury mixer, an internal mixer, or other rubber kneading machines.

<Raw Rubber Product Forming Step (Green Tire Forming Step in the Case of Tire)>

The raw rubber product forming step is as described above.

<Vulcanization Step>

The vulcanization step is as described above.

EXAMPLES

The present disclosure is specifically described with reference to examples, but the present disclosure is not limited to these examples.

(Acquisition of Trans-Prenyltransferase Gene Derived from *Manilkara zapota*)

In order to acquire a gene of a trans-prenyltransferase capable of synthesizing a high molecular weight trans-1,4-polyisoprene, a de novo assembly of the transcriptome of *Manilkara zapota*, which synthesizes a high molecular weight trans-1,4-polyisoprene, was performed to create contig sequences, which were then used to search for genes similar to the trans-prenyltransferase gene derived from *Arabidopsis thaliana*. Thus, two genes (MztPT1 [SEQ ID NO:1] and MztPT2 [SEQ ID NO:3]) were discovered.

In order to isolate the cDNAs of MztPT1 and MztPT2, various tissues of *Manilkara zapota* were collected and crushed into powder using a mortar and a pestle in liquid nitrogen, and total RNA was extracted using NucleoSpin RNA Plant and Fungi (MACHEREY-NAGEL, Duren, Germany). The obtained total RNA was dissolved in 50 μL of DEPC-treated water.

In order to acquire the cDNA of MztPT1, reverse transcription was performed using PrimeScriptII 1st strand cDNA Synthesis Kit (TaKaRa Bio) with the total RNA prepared from the petiole of *Manilkara zapota* as a template, and PCR was performed using the thus obtained 1st strand cDNA as a template with a primer set (3769 Fw:5'-ATGTTATTTTCCAGGGGATTTTC-3' (SEQ ID NO:7) and 3769 Rv:5'-CTACTTTGCTCTTGTAATGACTCTG-3' (SEQ ID NO:8)). The PCR product was electrophoresed in a 0.8% agarose gel, and the agarose gel containing the target band was cut out, collected, and then purified using Fast Gene Gel/PCR Extraction Kit (Nippon Genetics) (hereinafter, this operation is referred to as gel recovery).

Also, for the contig sequence corresponding to MztPT2, since the 5' terminal side was not assembled, a cDNA was synthesized using GeneRacer Kit (Invitrogen) with the total RNA prepared from a leaf of *Manilkara zapota* as a template, and PCR was performed using the cDNA as a template with a primer set (GeneRacer 5' Primer: 5'-CGACTGGAGCACGAGGACACTGA-3' (SEQ ID NO:9) and 4033 Rv GSP Race:5'-CTTGGGGAAAGTGGCCTTATTGCTGAC-3' (SEQ ID NO:10)) to amplify the 5' unknown region. Using this region as a template, nested PCR was performed to more specifically amplify the target sequence. The primers used here are GeneRacer 5' Nested Primer (5'-GGACACTGACATGGACTGAAGGAGTA-3' (SEQ ID NO:11)) and 4033 Rv GSP nested Race (5'-CTGCCTCACTAGCCCCTCCAACTATGG-3' (SEQ ID NO:12)). After the sequence of the amplified 5' unknown region was determined, PCR was performed using the 1st strand cDNA of the leaf as a template with a primer set (R4033 SLi XhoI Fw:5'-TCAGGGCGGATATCTCGAGATGGCCTTGAACCTTTTTC-3' (SEQ ID NO:13) and R4033 SLi KpnI Rv:5'-CTAGTGCGGCCGCGGTACCATTAATATTGACGGTTATTAATGTAATG-3' (SEQ ID NO:14)) designed based on the determined sequence data, to amplify the full-length MztPT2-coding sequence, which was then subjected to gel recovery.

Addition of dA to the PCR product containing the full-length MztPT1- or MztPT2-coding sequence was performed using 10×A-attachment mix (TOYOBO), each followed by subcloning into a pGEM-T Easy vector (Clontech), whereby pGEM-MztPT1 and pGEM-MztPT2 were prepared.

Since the chloroplast transit sequence prediction algorism ChloroP 1.1 (http://www.cbs.dtu.dk/services/ChloroP/) predicted that the amino acids 1-75 on the N-terminal side of MztPT1 corresponded to a chloroplast transit sequence, a gene sequence coding for the mutant enzyme MztPT1ΔN lacking this region was amplified by PCR. The template used here is pGEM-MztPT1, and the primer set used is MztPT1DN NdepColdISLi Fw (5'-TATCGAAGGTAGGCATATGGAGGAGCAACAGGATC-3' (SEQ ID NO:15)) and pCold 3769 KpnSLi Rv (5'-CGGATCCCTCGAGGGTACCC-TACTTTGCTCTTGTAATGACTCTG-3' (SEQ ID NO:16)). The amplified gene was subjected to gel recovery, followed by dA addition and then subcloning into a pGEM-T Easy vector, whereby pGEM-MztPT1ΔN was prepared.

With regard to MztPT2, a sequence (MztPT2opt) optimized according to the codon frequency of *Escherichia coli* was chemically synthesized. Also, since MztPT2 was found to have an amino acid sequence involved in membrane binding on the N-terminal side, a gene sequence (SEQ ID NO:6) coding for the mutant MztPT2ΔN lacking the amino acids 1-158 on the N-terminal side was amplified by PCR. The template used here is MztPT2opt, and the primer set used is tPT2opt 159 NdeSLi Fw (5'-CATATCGAAGGTAGGCATATGCTGGCACATGTTATTAGC-3' (SEQ ID NO:17)) and tPT2opt 159 KpnSLi Rv (5'-CGGATCCCTCGAGGGTACCTTAATACTGGCGGTTATTGATATAATG-3' (SEQ ID NO:18)). The amplified gene was subjected to gel recovery, followed by dA addition and then subcloning into a pGEM-T Easy vector, whereby pGEM-MztPT2ΔN was prepared.

(Preparation of *Escherichia coli* Expression Construct)

In order to clone each of the genes (MztPT1 and MztPT2) into the NdeI-KpnI site of the *Escherichia coli* expression plasmid pCold I, each gene sequence was amplified by PCR. The template used here is a pGEM-T Easy vector into which each gene was introduced. The primer set used to amplify MztPT1 is pCold 3769 NdeSLi Fw (5'-CATATCGAAGGTAGGCATATGTTATTTTCCAGGG-GATTTTC-3' (SEQ ID NO:19)) and pCold 3769 KpnSLi Rv (5'-CGGATCCCTCGAGGGTACCC-TACTTTGCTCTTGTAATGACTCTG-3' (SEQ ID NO:20)). The primer set used to amplify MztPT2 is 4033 NdeI Fw (5'-CATATGATGGCCTTGAACCTTTTTC-3' (SEQ ID NO:21)) and R4033 SLi KpnI Rv (5'-CTAGTGCGGCCGCGGTACCATTAATATTGACGGTT-ATTAATGTAATG-3' (SEQ ID NO:22)). The PCR products as well as pGEM-MztPT1ΔN and pGEM-MztPT2ΔN were digested with the restriction enzymes NdeI and KpnI. Gene fragments containing the protein-coding sequences were subjected to gel recovery. Likewise, the pCold I vector was digested with NdeI and KpnI, subjected to gel recovery, and then ligated to each coding sequence fragment using Ligation High (TOYOBO), whereby pCold I-MztPT1, pCold I-MztPT2, pCold I-MztPT1ΔN, and pCold I-MztPT2ΔN were prepared.

(Expression in *Escherichia coli* and Purification)

*Escherichia coli* BL21 was transformed using each of the prepared constructs (pCold I-MztPT1, pCold I-MztPT2, pCold I-MztPT1ΔN, and pCold I-MztPT2ΔN). Each transformed *Escherichia coli* was cultured, and enzyme expression was induced by adding IPTG. The cells were recovered by centrifugation and then disrupted by ultrasonic disruption, followed by centrifugation at 4° C. at 10000×g for 10 minutes to recover a soluble fraction and an insoluble fraction.

The MztPT1ΔN and MztPT2ΔN obtained as soluble proteins were each purified from the soluble fraction by $Ni^{2+}$-affinity chromatography using HisTrapHP (Cytiva). The eluted fraction containing each target protein was subjected to buffer exchange and concentration into an imidazole-free buffer (50 mM Tris-Cl (pH 7.5), 2 mM DTT) using the centrifugal ultrafiltration filter Amicon Ultra (Merck).

The activity of the purified MztPT1ΔN was measured using the reaction solution described below. After the reaction was performed at 30° C. for two hours, the product was extracted with butanol and then subjected to toluene/hexane extraction.

TABLE 1

| Reaction composition | (final) |
|---|---|
| Tris-Cl (pH 7.5) | 50 mM |
| DTT | 2 mM |
| $MgCl_2$ | 5 mM |
| Triton X-100 | 0.05% |
| FPP | 15 μM |
| [4-$^{14}$C] IPP (20 Ci/mol) | 50 μM |
| MztPT1ΔN | 0.5 μg |
| (up to) | 100 μL |

The activity of the purified MztPT2ΔN was measured using the reaction solution described below. After the reaction was performed at 30° C. for 16 hours, the product was extracted with butanol and then subjected to toluene/hexane extraction.

TABLE 2

| Reaction composition | (final) |
|---|---|
| Tris-Cl (pH 7.5) | 50 mM |
| DTT | 2 mM |
| $MgCl_2$ | 5 mM |
| FPP | 15 μM |
| [4-$^{14}$C] IPP (5 Ci/mol) | 50 μM |
| MztPT2ΔN | 10 μg |
| (up to) | 100 μL |

After the reaction, 200 μL of saturated saline was added and stirred to terminate the reaction. Thereto was added 1 mL of saturated saline/saturated n-butanol, and the mixture was agitated for one minute in a vortex mixer and then centrifuged at 15,000 rpm at room temperature for one minute, followed by collecting the upper butanol layer to extract a polyisoprenoid with a degree of polymerization that is universal to general organisms (approximately $C_{120}$ (molecular weight $1.81\times10^3$)). This extraction operation can extract polyisoprenoids with molecular weights up to about $3\times10^3$. Subsequently, 500 μL of toluene/hexane (1:1, vol/vol) was added to the aqueous layer, and the mixture was agitated for five minutes in a vortex mixer and centrifuged at 15,000 rpm at room temperature for one minute, followed by collecting the upper layer (toluene/hexane layer) to extract a polyisoprenoid product with a higher molecular weight. This toluene/hexane extraction process was performed twice, and a total of 1 mL of a toluene/hexane layer was extracted. An amount of 50 μL of the two extracts was added to 3 mL of Clear-sol, and the radioactivity was measured using a liquid scintillation counter (LD6500, BECKMAN COULTER). The background value was subtracted from the measured value. Since 50 μL out of 1 mL was measured, the difference was multiplied by 20 times to calculate the count as a whole.

(Determination of Molecular Weight of Product)

In order to analyze the degree of polymerization of the reaction product (polyprenyl diphosphate) contained in the butanol extract by reverse-phase TLC, acid phosphatase treatment was performed to convert the reaction product to polyprenyl alcohol. An amount of 500 μL of ultrapure water was added to the butanol extract and then centrifuged at 15,000 rpm at room temperature for one minute. Subsequently, the upper butanol layer was collected in another tube. The butanol was evaporated off using a centrifugal evaporator to concentrate the reaction product to 200 μL. The concentrated reaction product was reacted at 37° C. for 18 hours using a reaction composition containing an acid phosphatase (Potato acid phosphatase, Sigma) as shown below.

TABLE 3

| Acid phosphatase reaction solution | (final) |
|---|---|
| Acetic acid buffer | 40 mM |
| Methanol | 40% (v/v) |
| Triton X-100 | 0.1% (v/v) |
| Butanol extract | 200 μL |
| Potato acid phosphatase | 10 unit |
| | Up to 1 mL |

After the reaction, 120 μL of 5M NaOH was added to the reaction solution, and the mixture was maintained at 37° C.

for 30 minutes. In order to extract the resulting polyprenyl alcohol, 700 µL of pentane was added, and the mixture was stirred in a vortex mixer and centrifuged at 15,000 rpm at room temperature for one minute. Then, the upper pentane layer was collected. The pentane layer was washed with 500 µL of saturated saline and recovered. Then, the pentane layer was washed with 500 µL of ultrapure water and recovered. After the pentane was completely evaporated off using a centrifugal evaporator, the residue was again dissolved in 50 µL of pentane and developed on a TLC plate (HPTLC silica gel 60, RP-18, MERCK). The developing solvent used was acetone:water=39:1 (v/v). In the development, C55, C60, C85, and C90 polyprenyl alcohol samples were also developed. After the development, the positions of these samples were visualized by iodine coloration and then marked with an ink containing a $^{14}$C-labeled radioactive substance. The TLC plate covered with a plastic film was made in contact with an imaging plate for photosensitization. Thereafter, the signals were detected using a fluoro-image analyzer (FLA-2000, Fuji film).

The molecular weight of the product extracted with toluene/hexane was determined by GPC. Here, the GPC was performed under the measurement conditions described below.

(Activity Measurement Result)

Figure 3:
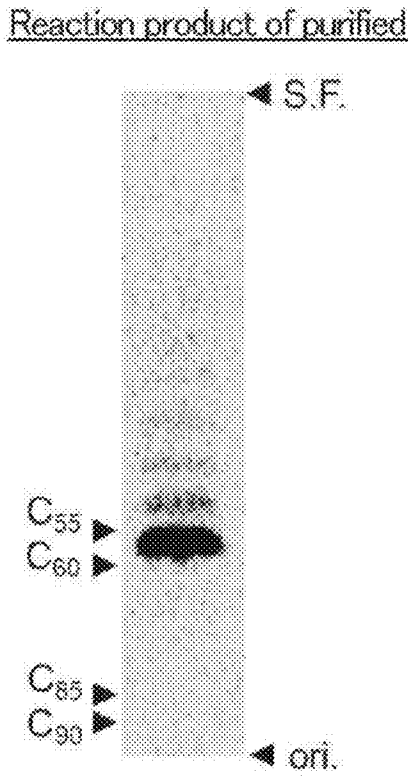
FIG. 3 is a diagram showing exemplary TLC results.

As the MztPT1 expressed in *Escherichia coli* was mostly fractionated into an insoluble fraction, this fraction was used to measure the activity. As a result, the MztPT1 product was extracted in the butanol extract layer, and reverse-phase TLC revealed that it was a $C_{55}$-$C_{60}$ (molecular weight: about 700 to 800) product. Similarly, the purified MztPT1ΔN product was also extracted in the butanol extract layer, and reverse-phase TLC revealed that it was a $C_{55}$-$C_{60}$ (molecular weight: about 700 to 800) product, as shown in FIG. 3.

Figure 4:
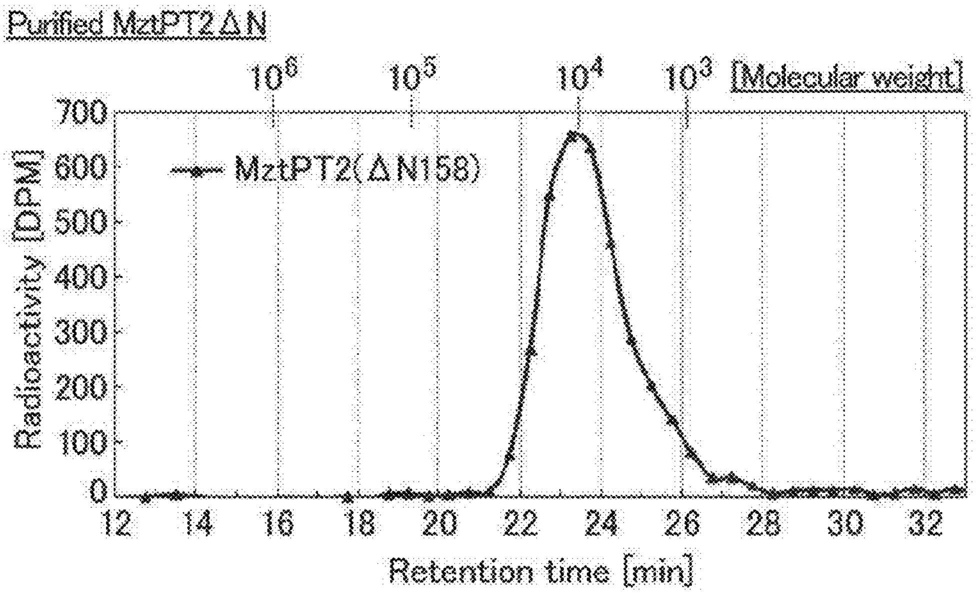
FIG. 4 is a diagram showing exemplary GPC results.

In contrast, the activity of MztPT2 was not confirmed. Also, as shown in FIG. 4, the purified MztPT2ΔN product was extracted in the toluene/hexane extract layer, and GPC analysis revealed that the product had a molecular weight of about $10^4$. It was thus found that the purified MztPT2ΔN was capable of producing a product with a molecular weight of $10^4$ or more when not bound to any lipid membrane. Here, the GPC was performed under the measurement conditions described below.

These results demonstrated that MztPT1 is capable of synthesizing a product with a molecular weight of less than $10^4$ when not bound to any lipid membrane; MztPT2 exhibits no activity when not bound to any lipid membrane; and MztPT2ΔN is capable of synthesizing a product with a molecular weight of $10^4$ or more when not bound to any lipid membrane.

Example 1

(Acquisition of Gene Coding for MLDP Membrane-Binding Peptide)

In order to fuse a membrane-binding peptide to MztPT2ΔN, acquisition of a membrane-binding domain derived from a major lipid droplet protein (MLDP) was performed.

(Acquisition of Total RNA Derived from *Chlamydomonas*)

RNA extraction was performed on the sta6 strain of *Chlamydomonas* (CC-4348, sta6-1 mt+) obtained from the *Chlamydomonas* Resource Center using RNAiso (TaKaRa BIO). To *Chlamydomonas* cells stored at −80° C. was added 1 mL of RNAiso Plus, and the mixture was vortexed for five minutes and centrifuged at 4° C. at 12,000×g for three minutes. After the supernatant was collected, 200 µL of chloroform was added, and the mixture was mixed in a vortex mixer. After standing still at room temperature for five minutes, the mixture was centrifuged at 4° C. at 12,000×g for 15 minutes. The upper aqueous layer was collected, and 500 µL of isopropanol was added and mixed in a vortex mixer. After standing still at room temperature for 10 minutes, the mixture was centrifuged at 4° C. at 12,000×g for 15 minutes to precipitate RNA, and the upper layer was discarded. Then, 750 µL of 75% ethanol was added to wash the pellet, and centrifugation was performed at 4° C. at 12,000×g for five minutes to remove the upper layer, followed by standing still at room temperature for five minutes for drying. Finally, the dried product was dissolved in 50 µL of DEPC-treated water.

DNase treatment was performed to remove contaminating genomic DNA from the extracted total RNA. In the DNase treatment, DNase I recombinant, RNase-free (Roche) was used, and a reaction solution as described below was prepared and incubated at 37° C. for 30 minutes.

After the reaction, 350 µL of DEPC-treated water and 400 µL of phenol were added and mixed, and the mixture was centrifuged at room temperature at 15,000 rpm for 15 minutes. To the collected upper layer were added 30 µL of 3M NaOAc and 660 µL of ethanol and mixed, followed by standing still at −30° C. for one hour. The mixture was centrifuged at 4° C. at 15,000 rpm for 15 minutes to precipitate RNA, and the upper layer was discarded. Then, 700 µL of 70% ethanol was added to wash the pellet, and centrifugation was performed at 4° C. at 12,000×g for five minutes to remove the upper layer, followed by standing still at room temperature for five minutes for drying. The obtained precipitate was dissolved in 50 µL of DEPC-treated water.

(Acquisition of MLDP cDNA Derived from *Chlamydomonas*)

The cDNA of MLDP (Accetion no. PNW79191.1) from *Chlamydomonas* was amplified by PCR using, as a template, a cDNA synthesized from the total RNA of *Chlamydomonas* using Fast Gene Scriptase II (NIPPON Genetics EUROPE), with the primers: MLDP 1 EcoRV Fw (5'-AGTCAGA-TATCTCATGGCCGAGTCTGCTG-3' (SEQ ID NO:23)) and MLDP noend 765 BamHI Rv (5'-TGACTG-GATCCTCGGGGCCGGGTTGCAC-3' (SEQ ID NO:24)). The obtained nucleotide sequence of MLDP derived from *Chlamydomonas* is shown in SEQ ID NO:5. The amplified gene was subjected to gel recovery, followed by dA addition and subcloning into a pGEM-T Easy vector, whereby pGEM-MLDP was prepared.

(Construction of Vector in which Gene with Fused MLDP and Linker Sequences is Introduced)

In order to express a fusion protein in which MLDP was fused to MztPT2ΔN by a linker sequence consisting of 24 amino acids (N-terminal-TGNSADGGGGSGGSGGSGGG-STQG-C-terminal (SEQ ID NO:25)) in a cell-free translation system, a gene in which the MLDP and liker sequences were fused was first introduced into a restriction enzyme site of pEU-E01-His-TEV-MCS-N2 (CellFree Science, Matsuyama, Japan, hereinafter, referred to as pEU-N2).

The MLDP sequence was amplified by PCR using pGEM-MLDP as a template with a primer set (MLDP-linker EcoRV 1 Fw:5'-AGTCAGATATCTCATGGCCGAGTCTGCTG-GAAAG-3' (SEQ ID NO:26) and MLDP+Linker MLDP 765 Rv:5'-CCGTCAGCGGAAT-TACCGGTGGGGCCGGGTTGCACG-3' (SEQ ID NO:27)). Next, the liker sequence was amplified by PCR using pGFP-L4HPB containing the linker sequence as a template with a primer set (MLDP+Linker Linker 1 Fw:5'-

CGTGCAACCCGGCCCCACCGGTAATTCCGCTGACGG-3' (SEQ ID NO:28) and MLDP-linker 837 BamHI Rv:5'-TGACTGGATCCGACCCTTGGGTCGATCCTCC-3' (SEQ ID NO:29)). The two PCR products were mixed to prepare a solution, and PCR was performed using the solution as a template with a primer set (MLDP-linker EcoRV 1 Fw:5'-AGTCAGATATCTCATGGCCGAGTCTGCTGGAAAG-3' (SEQ ID NO:30) and MLDP-linker 837 BamHI Rv:5'-TGACTGGATCCGACCCTTGGGTCGATCCTCC-3' (SEQ ID NO:31)) to prepare a gene in which the MLDP- and liker-coding sequences were fused. This fusion gene was digested with the restriction enzymes EcoRV and BamHI and subjected to gel recovery. The resulting fragment was mixed with pEU-N2 that had been digested with the same restriction enzyme set and subjected to gel recovery, and they were ligated using Ligation High, whereby pEU-N2-MLDP-linker was prepared.

(Construction of Vector into which MLDP-Fused MztPT2ΔN is Introduced)

In order to introduce into pEU-N2 a gene coding for a protein in which MLDP, a linker, and MztPT2ΔN were fused in the stated order from the N-terminal side to the C-terminal side (MLDP-MztPT2ΔN), the Mztpt2ΔN gene was amplified by PCR using pGEM-Mztpt2ΔN as a template with a primer set (MztPT2 159 SmaI Fw:5'-AGTCACCCGGGCTAGCCCATGTAATCAGCAACATCAAG-3' (SEQ ID NO:32) and MztPT2 1422 NotI Rv:5'-TGACTGCGGCCGCGTTAATATTGACGGTTATTAATG TAATGAG-3' (SEQ ID NO:33)). The amplified gene was purified and then digested with the restriction enzymes SmaI and NotI and subjected to gel recovery. The resulting fragment was mixed with pEU-N2-MLDP-linker that had been digested with the same restriction enzyme set and subjected to gel recovery, and they were ligated using Ligation High, whereby pEU-N2-MLDP-MztPT2ΔN was prepared.

(Acquisition of Lipid Droplets Derived from *Chlamydomonas*)

(Culture of *Chlamydomonas*)

The sta6 strain of *Chlamydomonas* (CC-4348, sta6-1 mt+) and its parent strain, cw15 strain (CC-4349, cw15 mt+), were obtained from the *Chlamydomonas* Resource Center. Liquid culture of *Chlamydomonas* was performed at 22° C. under continuous light with a photon flux density of 100 $\mu mol\ m^{-2}s^{-1}$ in rotary culture at 120 rpm. The medium used was a TAP liquid medium, and passaging was performed every week.

Growing under nitrogen-deficient conditions is necessary to purify lipid droplets (LD) for use in a cell-free translation system. In this case, 5 mL of the culture liquid obtained after 7 days of liquid culture in the above-described liquid medium was added to 95 mL of the below-described HSM liquid medium and cultured at a photon flux density of 30 $\mu mol\ m^{-2}s^{-1}$ at 120 rpm and 22° C. A few days later, 2 μL of a sample was placed in a counting chamber (Sunlead Glass Corp.) and observed with a BX40 microscope (OLYMPUS) to calculate the cell density. Once the density reached 2.6 (+1.2)x$10^6$/mL, centrifugation was performed at 2,000×g for five minutes to collect the *Chlamydomonas* cells. Subsequently, the cells were re-suspended in 100 mL of a HSM (N-free) medium and cultured again. Two days later, 1.3 mL of 1.5M KOAc was added and cultured for another two days. The resulting culture liquid was collected and centrifuged at 2,000×g for five minutes to remove the medium. The residue was flash frozen in liquid nitrogen and then stored at −80° C.

TABLE 4

| | volume |
|---|---|
| **HSM medium** | |
| No. 1 stock liquid | 10 mL |
| No. 2 stock liquid | 10 mL |
| 2M MOPS | 10 mL |
| Hunter's trace elements | 10 mL |
| Ultrapure water | up to 1 L |
| **No. 1 stock liquid** | |
| $NH_3Cl$ (except for N-free) | 50 g |
| $MgSO_4 \cdot 7H_2O$ | 2.0 g |
| $CaCl_2 \cdot 2H_20$ | 1.0 g |
| $CH_3COOK$ | 196.28 g |
| Ultrapure water | up to 1 L |
| **No. 2 stock liquid** | |
| $K_2HPO_4$ | 144 g |
| $KH_2PO_4$ | 72 g |
| Ultrapure water | up to 1 L |
| **Hunter's trace elements** | |
| $Na_2$-EDTA | 5.0 g |
| $ZnSO_4 \cdot 7H_2O$ | 2.2 g |
| $H_3BO_3$ | 1.14 g |
| $MnCl_2 \cdot 4H_2O$ | 0.51 g |
| $CoCl_2 \cdot 6H_2O$ | 0.16 g |
| $CuSO_4 \cdot 5H_2O$ | 0.16 g |
| $(NH_4)_6Mo_7O_{24} \cdot 4H_2O$ | 0.11 g |
| $FeSO_4 \cdot 7H_2O$ | 0.50 g |
| KOH | 1.6 g |
| Ultrapure water | up to 1 L |

(Preparation of Lipid Droplets Derived from *Chlamydomonas*)

The *Chlamydomonas* cells cultured in 5 mL of Buffer A shown below were suspended and then allowed to stand still for five minutes. Thereafter, 30 ml of Buffer B was added, and the mixture was centrifuged at 20,000×g at 4° C. for 30 minutes. The top layer containing LD (lipid droplets) was collected with a pipette and suspended with 3 mL of Buffer B, and the suspension was centrifuged at 1,000×g at 4° C. for 10 minutes. Then, the lower layer solution was collected with a syringe to separate and remove a neutral lipid layer mainly derived from broken LD. The collected lower layer suspension was centrifuged at 20,000×g at 4° C. for 30 minutes, and the lower aqueous phase was removed. Then, the LD layer remaining in the tube was re-suspended with 60 μL of TD buffer [0.1 M Tris-Cl (pH 7.5), 5 mM DTT]. The protein concentration of the LD suspension was measured by the Bradford method using an absorbance microplate reader (SpectraMax ABS Plus, Molecular Devices) to provide an indication of the amount of LD to be added to the cell-free expression system. Observation with a fluorescence microscope BX40 (OLYMPUS) was also performed to confirm the collected LD.

TABLE 5

| | Buffer A | | Buffer B | |
|---|---|---|---|---|
| | volume | final | volume | final |
| 1M Sucrose | 30 mL | 0.6M | 20 mL | 0.4M |
| 0.1M EDTA (pH 7.5) | 0.5 mL | 1 mM | 0.5 mL | 1 mM |
| 1M Hepes-KOH (pH 7.5) | 1.25 mL | 25 mM | 1.25 mL | 25 mM |
| SDW | up to 50 mL | | up to 50 mL | |

(Cell-Free Expression)

(Synthesis and Extraction of mRNA Used in Cell-Free Expression)

Using WEPRO7240H Expression Kit (CellFree Sciences, Matsuyama, Japan), mRNA was synthesized from the prepared construct. A reaction was performed using the below-described composition at 37° C. for three hours. The reaction was followed by ethanol precipitation, and the obtained pellet was dissolved in 25 μL of 1×DB buffer. The recovered mRNA was stored at −80° C.

TABLE 6

| | volume | final |
|---|---|---|
| 5× Transcription Buffer | 10 μL | 1× |
| 25 mM NTP mix | 6 μL | 3 mM |
| RNase Inhibitor (80,000 unit/mL) | 0.5 μL | |
| SR6 RNA Polymerase | 0.75 μL | 4 unit/50 μL |
| Plasmid | | 5 μg/50 μL |
| SDW | up to 50 μL | |

(Introduction of Protein onto Lipid Droplets in Cell-Free Translation System)

For translation/folding-coupled introduction of a foreign protein into LD in a cell-free translation system, a translation reaction was performed using a wheat germ-derived cell-free protein expression kit (WEPRO7240H Expression Kit, CellFree Sciences).

To 7.5 μL of the prepared mRNA was added 15 μL of 1×DB buffer to prepare a mRNA premix. Then, a translation reaction solution with the following composition was prepared.

TABLE 7

| | volume |
|---|---|
| SDW | |
| 4 × DB | 6.25 μL |
| LD | X μL |
| Creatine Kinase | 2 μL |
| RNase inhibitor | 1 μL |
| mRNA Premix | 17.5 μL |
| Wepro | 12.5 μL |
| total | 50 μL |

An amount of 650 μL of sterile ultrapure water was added to a plastic tube (PP container, 4.5 mL, 5-094-02, AS ONE). A dialysis cup (MWC012000, COSMO BIO CO., LTD.) was placed in the tube such that air did not enter the dialysis membrane, and then allowed to stand still for 10 minutes or longer. Then, the sterile ultrapure water was discarded from the tube, 650 μL of 1×DB buffer was added as an external fluid, and 50 μL of the prepared translation reaction solution was added as an internal fluid into the dialysis cup. The dialysis cup was placed in the plastic tube such that air did not enter the dialysis membrane, and the cup was covered with a parafilm, followed by reaction at 26° C. for five hours. After the reaction, the external fluid was replaced with new 1×DB buffer, and 5 μL of the mRNA premix was added to the internal fluid, followed by further reaction for 13 hours. After completion of the reaction, the reaction solution was collected, a 50-μL portion of which was then transferred to a 1.5-mL tube, and 50 μL of TD buffer (+20% (w/v) glycerol) was added, followed by centrifugation at 20,000×g at 4° C. for 30 minutes. From the LD fraction, soluble fraction, and precipitated fraction thus obtained, the LD fraction and soluble fraction were transferred together to a new tube, followed by further centrifugation at 20,000×g at 4° C. for 30 minutes. The aqueous layer of the centrifuged solution was drawn out and collected in another tube (as a soluble fraction) using a syringe (needle, NN-2719S; 1 mL tuberculin syringe, SS-01T, Terumo, Tokyo, Japan), while 100 μL of TD buffer (+10% (w/v) glycerol) was added to the LD layer remaining in the tube, and the mixture was further centrifuged at 20,000×g at 4° C. for 30 minutes (washing operation). The aqueous layer was drawn out using the syringe, and the rest was suspended with 100 μL of TD buffer containing a protease inhibitor cocktail (cOomplete mini EDTA free Protease Inhibitor Cocktail Tablets, Roche). This suspension was used as a purified LD fraction. Separately, the tube from which the LD layer and aqueous layer were initially removed (the precipitated fraction was left) was re-suspended with 100 μL of TD buffer, and this suspension was used as a precipitated fraction.

(Enzyme Activity Measurement)

In order to measure the prenyltransferase activity of the suspension of the purified LD into which a foreign protein had been introduced in a cell-free translation system, it was shaken with the below-described reaction composition in a bath at 30° C. for 18 hours. However, in order to align the assay input of the purified LD, the amount of the LD suspension to be added to the reaction system was adjusted so that it contained 2 μg of proteins. Also, a sample in which ultrapure water was added instead of the purified LD solution to measure the background of the prenyltransferase activity was prepared and shaken as described above.

TABLE 8

| | final |
|---|---|
| Tris-HCl (ph 7.5) | 50 mM |
| DTT | 2 mM |
| $MgCl_2$ | 5 mM |
| FPP | 15 μM |
| [4-$^{14}$C] IPP (5 Ci/mol) | 50 μM |
| Purified LD solution | X μL |
| Ultrapure water | up to 100 μL |

After the reaction, 200 μL of saturated saline was added and stirred to terminate the reaction. Thereto was added 1 mL of saturated saline/saturated n-butanol, and the mixture was agitated for one minute in a vortex mixer and then centrifuged at 15,000 rpm at room temperature for one minute, followed by collecting the upper butanol layer to extract a polyisoprenoid with a degree of polymerization that is universal to general organisms (approximately $C_{120}$ (molecular weight $1.81\times10^3$)). This extraction operation can extract polyisoprenoids with molecular weights up to about $3\times10^3$. Subsequently, 500 μL of toluene/hexane (1:1, vol/vol) was added to the aqueous layer, and the mixture was agitated for five minutes in a vortex mixer and centrifuged at 15,000 rpm at room temperature for one minute, followed by collecting the upper layer (toluene/hexane layer) to extract a polyisoprenoid product with a higher molecular weight. This toluene/hexane extraction process was performed twice, and a total of 1 mL of a toluene/hexane layer was extracted. An amount of 50 μL of the two extracts was added to 3 mL of Clear-sol, and the radioactivity was measured using a liquid scintillation counter (LD6500, BECKMAN COULTER). The background value was subtracted from the measured value. Since 50 μL out of 1 mL was measured, the difference was multiplied by 20 times to calculate the count of the total extract.

(Determination of Product Chain Length by Gel Permeation Chromatography (GPC))

The solvent in the extracted toluene/hexane extract was evaporated off using an evaporator, and then 190 μL of tetrahydrofuran (THF) was added. The mixture was passed through a filter unit (MS PTFE Syringe Filter, Pore Size: 0.45 μm, Membrane Solutions) connected to a syringe and transferred to a lightproof bottle to remove aggregates, etc. A 50-μL portion of the resulting filtrate was separated and analyzed by GPC-8020 (TOSOH). The analysis conditions are as follows.

Column Structure:

Guard column; TSKguardcolumn MP (XL) (TOSOH)

Solvent column; TSKgel Multipore HXL-M (TOSOH) (two columns connected)

Measurement temperature: 40° C.

Elution solvent: THE (tetrahydrofuran)

Flow rate: 0.8 mL/min

Detection: differential refractometer

Molecular weight standard: polystyrene standards

The THF flowed out of the column was collected every 30 seconds from 12 to 30 minutes after the injection. To each collection was added 3 mL of Clear sol, and then the radioactivity was measured using a liquid scintillation counter.

Comparative Example 1

Comparative Example 1 was performed as in Example 1, except that the MztPT2ΔN gene was directly introduced into the cell-free expression vector to prepare a vector that expresses it without fusing with MLDP.

PCR amplification was performed using pGEM-MztPT2 as a template with a primer set (MztPT2 159 SmaI Fw:5'-AGTCACCCGGGCTAGCCCATGTAATCAGCAACATCAAG-3' (SEQ ID NO:34) and MztPT2 1422 NotI Rv:5'-TGACTGCGGCCGCGTTAATATTGACGGTTATTAATGTAATGAG-3' (SEQ ID NO:35)). The PCR product was purified and then digested with the restriction enzymes SmaI and NotI and subjected to gel recovery. The resulting fragment was mixed with pEU-N2 that had been digested with the same restriction enzyme set and subjected to gel recovery, and they were ligated using Ligation High, whereby pEU-N2-MztPT2ΔN was prepared.

In the construction in which only MLDP was introduced into pEU-N2, the sequence amplified in the above (Acquisition of MLDP cDNA derived from *Chlamydomonas*) was digested with EcoRV and BamHI, subjected to gel recovery, and then mixed with pEU-N2 that had been digested with the same restriction enzyme set and subjected to gel recovery, and they were ligated using Ligation High, whereby pEU-N2-MLDP was prepared.

(Activity Measurement Result)

As a result of the activity measurement, no product was extracted in both the butanol extract layer and the toluene/hexane layer in Comparative Example 1, while product counts were observed in the toluene/hexane layer in Example 1.

Figure 5:
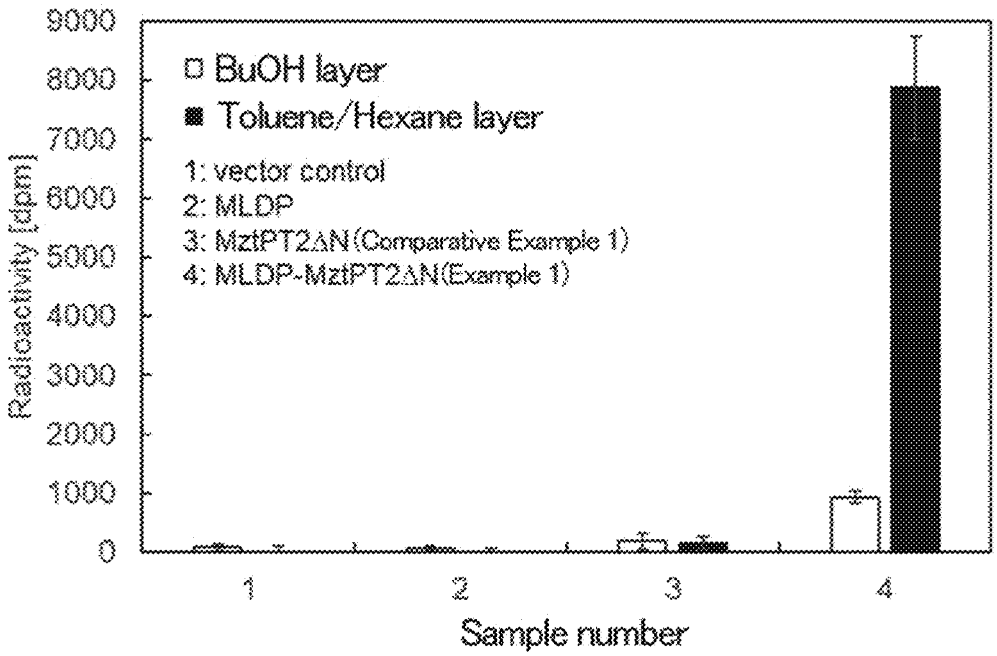
FIG. 5 is a diagram showing exemplary activity measurement results.
Figure 6:
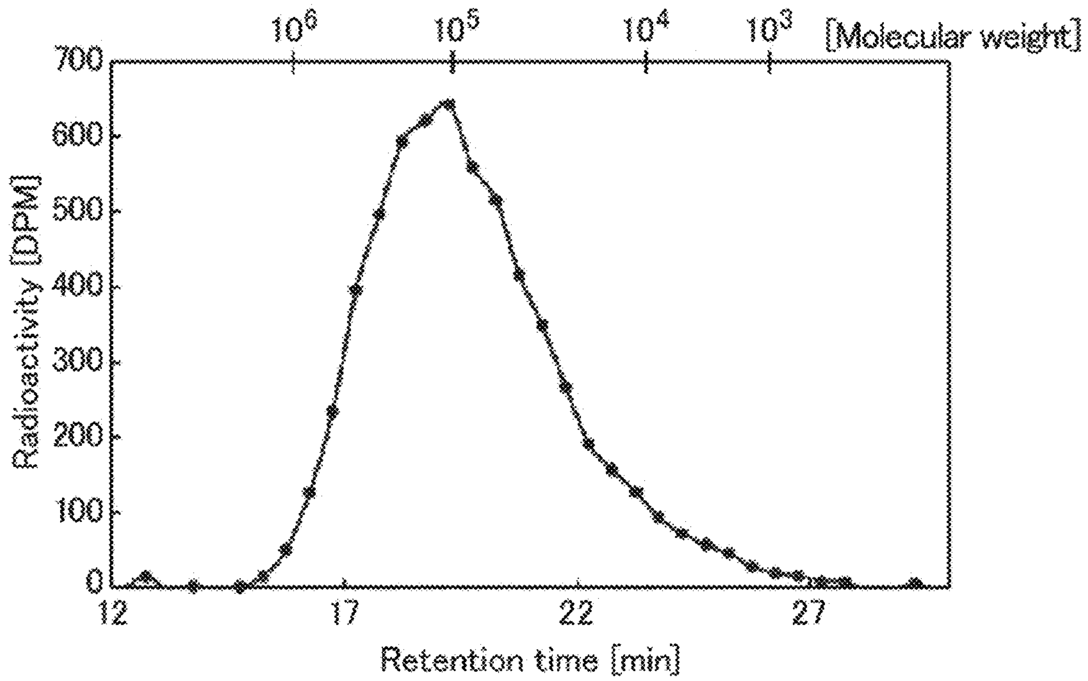
FIG. 6 is a diagram showing exemplary GPC results.

The molecular weight of the product extracted in the toluene/hexane layer was measured, and it was found that a trans-polyisoprenoid with a molecular weight of more than $10^5$ was produced in Example 1, as shown in FIG. 6. In Comparative Example 1 (sample 3 in FIG. 5), it is considered that since MztPT2ΔN does not have a membrane-binding ability, the enzyme did not bind onto LD, and no activity was observed. In Example 1 (sample 4 in FIG. 5), it is considered that MztPT2ΔN was fused to the MLDP membrane-binding peptide to obtain a membrane-binding ability, and therefore, the enzyme became able to bind onto LD. It was also found that by binding to the membrane, the enzyme synthesizes a product with a higher molecular weight than when not bound to any lipid membrane.

Comparative Example 2

Comparative Example 2 was performed as in Example 1, except that the protein to be fused to the MLDP membrane-binding peptide was changed from MztPTΔ2 to MztPT1.

The MzTPT1 gene was amplified by PCR using pGEM-Mztpt1 as a template with a primer set (MztPT1 1 SmaI Fw:5'-AGTCACCCGGGATGTTATTTTCCAGGGGATTTTCTCGG-3' (SEQ ID NO:36) and MztPT1 1263 NotI Rv:5'-TGACTGCGGCCGCGCTACTTTGCTCTTGTAATGACTCTG-3' (SEQ ID NO:37)). The amplified gene was purified and then digested with the restriction enzymes SmaI and NotI and subjected to gel recovery. The resulting fragment was mixed with pEU-N2-MLDP-linker that had been digested with the same restriction enzyme set and subjected to gel recovery, and they were ligated using Ligation High, whereby pEU-N2-MLDP-MztPT1 was prepared.

Example 2

In Example 2, full-length MztPT2 was cloned into the cell-free expression vector so that the enzyme was expressed while maintaining the membrane-binding peptide originally possessed by MztPT2, and then the enzyme was bound to LD.

PCR amplification was performed using pGEM-MztPT2 as a template with a primer set (MztPT2 1 SmaI Fw:5'-AGTCACCCGGGATGGCCTTGAACCTTTTTC-3' (SEQ ID NO:38) and MztPT2 1422 NotI Rv:5'-TGACTGCGGCCGCGTTAATATTGACGGTTATTAATGTAATGAG-3' (SEQ ID NO:39)). The PCR product was purified and then digested with the restriction enzymes SmaI and NotI and subjected to gel recovery. The resulting fragment was mixed with pEU-N2 that had been digested with the same restriction enzyme set and subjected to gel recovery, and they were ligated using Ligation High, whereby pEU-N2-MztPT2 was prepared.

(Result)

Figure 7:
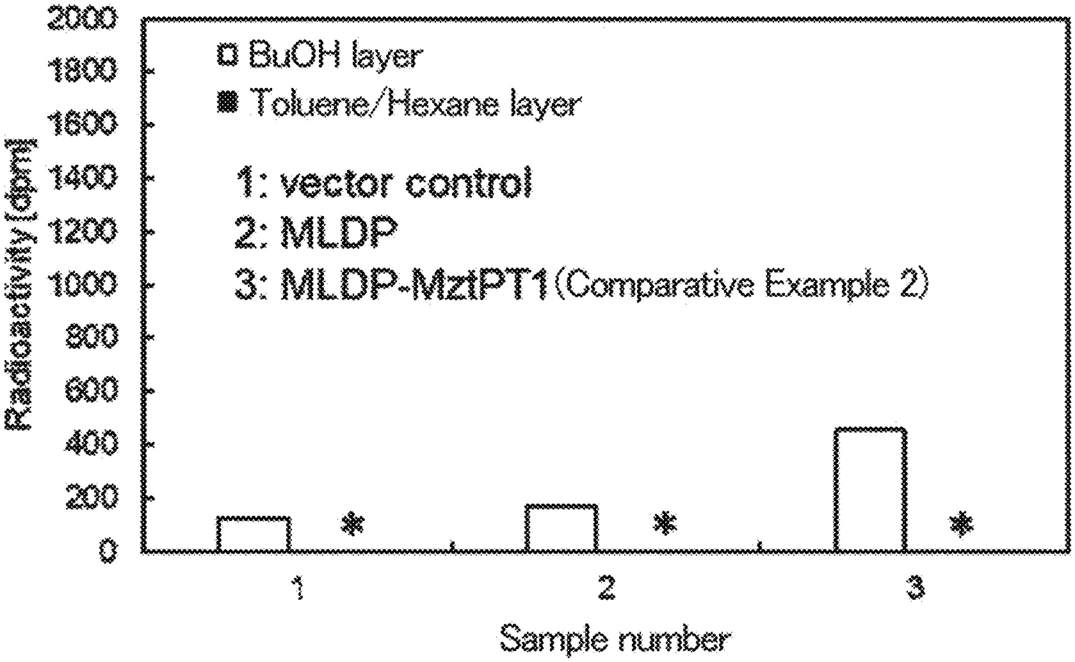
FIG. 7 is a diagram showing exemplary activity measurement results.
Figure 8:
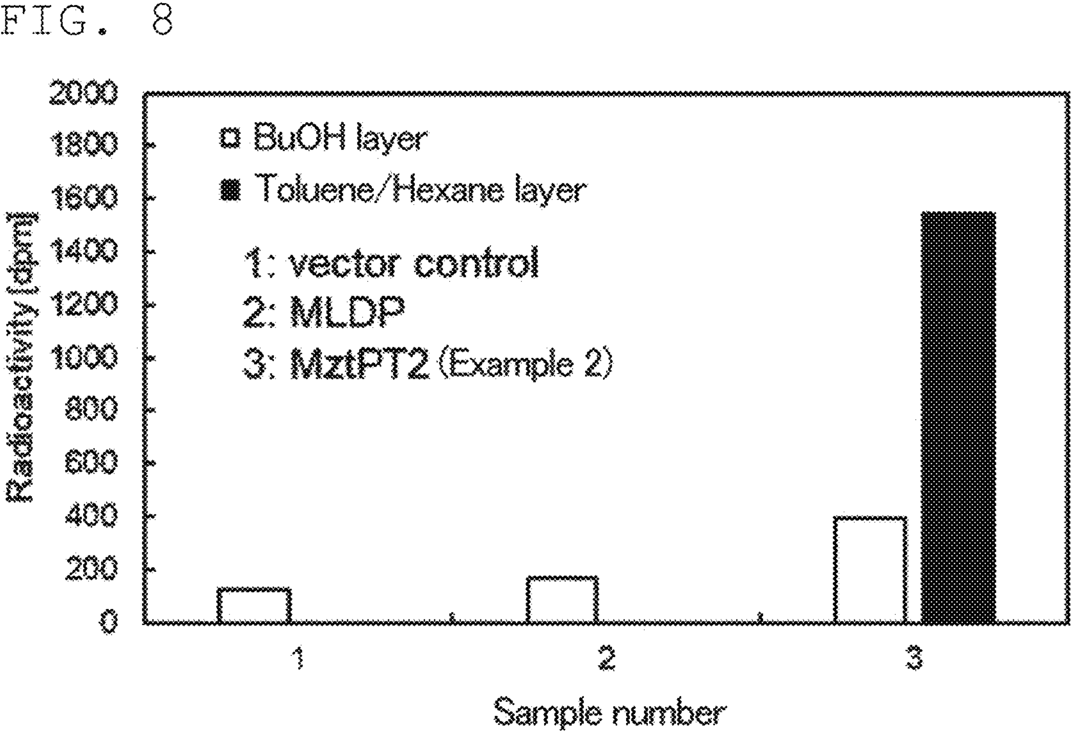
FIG. 8 is a diagram showing exemplary activity measurement results.

In Comparative Example 2 (sample 3 in FIG. 7), MLDP-MztPT1 bound to LD showed activity only in the butanol layer and had no activity in the toluene/hexane layer. In contrast, full-length MztPT2 (Example 2, sample 3 in FIG. 8), like MztPT2ΔN-MLDP, had activity in the toluene-hexane layer. This demonstrated that binding to a membrane a tPT only capable of producing a product of less than $10^4$ when not bound to any lipid membrane does not increase the molecular weight of the product, and that in order to bind to a membrane and produce a product with a higher molecular weight, a tPT capable of producing a product with a molecular weight of $10^4$ or more when not bound to any lipid membrane needs to be bound to a membrane. It was also found that as the original membrane-binding domain of MztPT2 gave similar results to those obtained by fusion to the MLDP-derived membrane-binding peptide, the membrane-binding peptide may have any amino acid sequence as long as it has a membrane-binding ability.

Example 3

Example 3 was performed as in Example 1, except that the lipid membrane was changed from the *Chlamydomonas*- derived LD to microsomes contained in a wheat germ-derived cell-free expression solution.

In a wheat germ-derived cell-free protein expression system, a reaction solution contains microsomes (membrane vesicles derived from organelle membranes, including endoplasmic reticula) derived from a wheat germ extract. If the target protein has a membrane-binding domain or a highly hydrophobic domain, the protein expressed in the cell-free translation system may bind to the microsomal membrane in the reaction system. Hence, MLDP-MztPT2ΔN was expressed using the wheat germ-derived cell-free protein expression kit in the same manner as in the system for introduction of a protein into LD, except that no LD was added to the reaction system. After the translation reaction, the reaction solution was collected, a 50-μL portion of which was then transferred to a 1.5-mL tube, and 50 μL of TD buffer (+20% (w/v) glycerol) was added, followed by centrifugation at 20,000×g at 4° C. for 30 minutes. From the soluble fraction and precipitated fraction thus obtained, the soluble fraction was transferred to a new tube, followed by further centrifugation at 100,000×g at 4° C. for 30 minutes. The aqueous layer of the centrifuged solution was collected in another tube (as a soluble fraction), and the precipitated fraction remaining in the tube was suspended with 100 μL of TD buffer (+10% (w/v) glycerol), followed by centrifugation at 100,000×g at 4° C. for 30 minutes (washing operation). The aqueous layer was removed, and the rest was suspended with 100 μL of TD buffer containing a protease inhibitor cocktail (cOomplete mini EDTA free Protease Inhibitor Cocktail Tablets, Roche). This suspension was used as a microsome fraction.

(Result)

Figure 9:
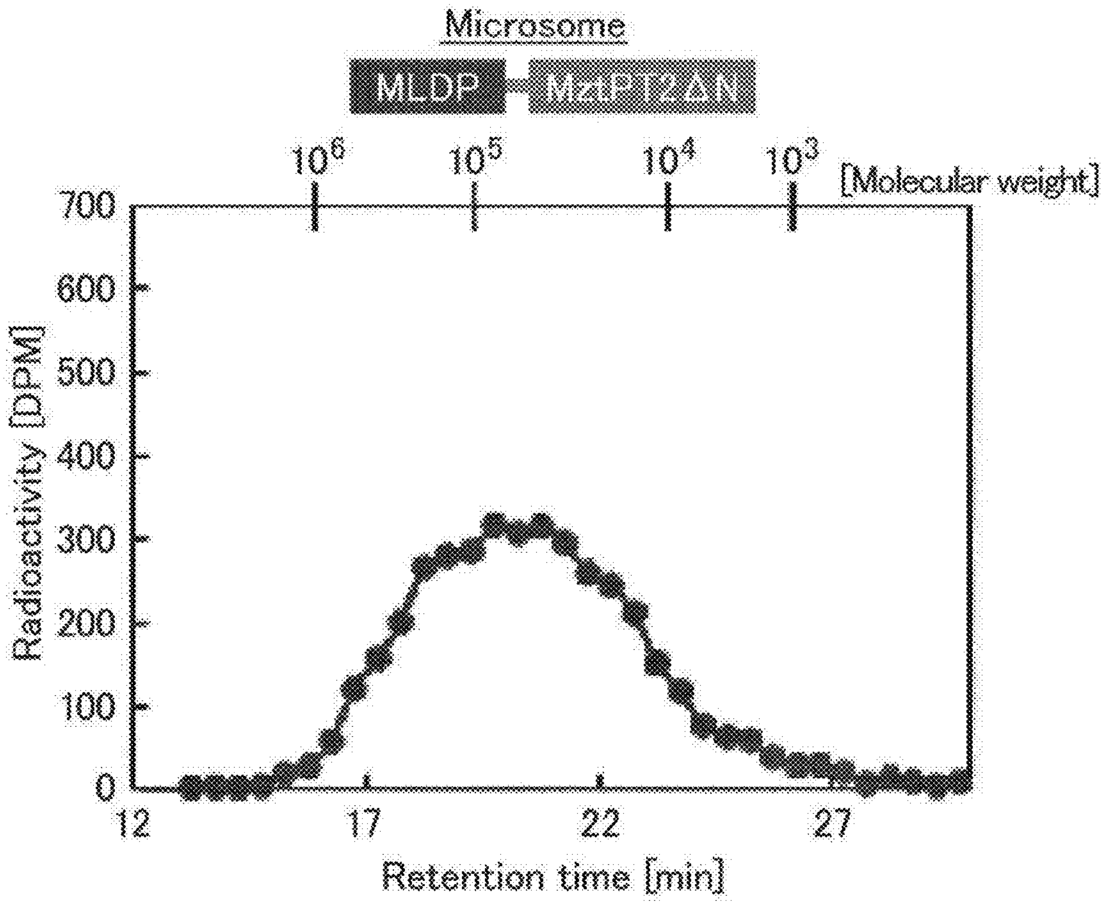
FIG. 9 is a diagram showing exemplary GPC results.

In Example 3, in which the lipid membrane was changed from the *Chlamydomonas*-derived LD to the microsome, the production of a trans-polyisoprenoid with a molecular weight of more than $10^5$ was still observed, as shown in FIG. 9.

Exemplary embodiments of the present disclosure include:

Embodiment 1. A method for producing a trans-polyisoprenoid, the method including binding to a lipid membrane in vitro a trans-prenyltransferase (tPT) family protein capable of producing a product with a molecular weight of $10^4$ or more when not bound to any lipid membrane.

Embodiment 2. The method for producing a trans-polyisoprenoid according to Embodiment 1, wherein the tPT family protein is a protein which has a membrane-binding domain and which can produce a product with a molecular weight of $10^4$ or more in an aqueous layer when not bound to any lipid membrane after solubilization.

Embodiment 3. The method for producing a trans-polyisoprenoid according to Embodiment 1 or 2, wherein the tPT family protein is derived from a trans rubber-producing plant.

Embodiment 4. The method for producing a trans-polyisoprenoid according to Embodiment 1 or 2, wherein the tPT family protein is derived from *Manilkara zapota*.

Embodiment 5. The method for producing a trans-polyisoprenoid according to Embodiment 1, wherein the tPT family protein is a protein to which an ability to bind to the lipid membrane has been imparted by fusing a membrane-binding peptide to a protein having no membrane-binding domain and capable of producing a product with a molecular weight of $10^4$ or more in an aqueous layer when not bound to any lipid membrane.

Embodiment 6. The method for producing a trans-polyisoprenoid according to Embodiment 5, wherein the protein having no membrane-binding domain and capable of producing a product with a molecular weight of $10^4$ or more in an aqueous layer when not bound to any lipid membrane is derived from a trans rubber-producing plant.

Embodiment 7. The method for producing a trans-polyisoprenoid according to any one of Embodiments 1 to 6, wherein the binding includes performing protein synthesis in the presence of both the lipid membrane and a cell-free protein synthesis solution containing an mRNA coding for the tPT family protein to bind the tPT family protein to the lipid membrane.

Embodiment 8. A method for producing a pneumatic tire, the method including: kneading a trans-polyisoprenoid obtained by the method for producing a trans-polyisoprenoid according to any one of Embodiments 1 to 7 with an additive to obtain a kneaded mixture; forming a green tire from the kneaded mixture; and vulcanizing the green tire.

Embodiment 9. A method for producing a rubber product, the method including: kneading a trans-polyisoprenoid obtained by the method for producing a trans-polyisoprenoid according to any one of Embodiments 1 to 7 with an additive to obtain a kneaded mixture; forming a raw rubber product from the kneaded mixture; and vulcanizing the raw rubber product.

Embodiment 10. A vector, containing a gene coding for a trans-prenyltransferase (tPT) family protein capable of producing a product with a molecular weight of $10^4$ or more when not bound to any lipid membrane.

Embodiment 11. A transgenic organism into which the vector according to Embodiment 10 has been introduced.

Embodiment 12. A method for producing a trans-polyisoprenoid using the transgenic organism according to Embodiment 11.

Embodiment 13. A method for producing a pneumatic tire, the method including: kneading a trans-polyisoprenoid obtained from the transgenic organism according to Embodiment 11 with an additive to obtain a kneaded mixture; forming a green tire from the kneaded mixture; and vulcanizing the green tire.

Embodiment 14. A method for producing a rubber product, the method including: kneading a trans-polyisoprenoid obtained from the transgenic organism according to Embodiment 11 with an additive to obtain a kneaded mixture; forming a raw rubber product from the kneaded mixture; and vulcanizing the raw rubber product.

SEQUENCE LISTING FREE TEXT

SEQ ID NO:1: nucleotide sequence of gene coding for tPT1 derived from *Manilkara zapota* (MztPT1)

SEQ ID NO:2: amino acid sequence of tPT1 derived from *Manilkara zapota* (MztPT1)

SEQ ID NO:3: nucleotide sequence of gene coding for tPT2 derived from *Manilkara zapota* (MztPT2)

SEQ ID NO:4: amino acid sequence of tPT2 derived from *Manilkara zapota* (MztPT2)

SEQ ID NO:5: nucleotide sequence of gene coding for MLDP derived from *Chlamydomonas*

SEQ ID NO:6: nucleotide sequence of MztPT2ΔN which is tPT2 derived from *Manilkara zapota* from which membrane-binding peptide domain has been deleted SEQ ID NO:7: Primer 1
SEQ ID NO:8: Primer 2
SEQ ID NO:9: Primer 3
SEQ ID NO:10: Primer 4
SEQ ID NO:11: Primer 5
SEQ ID NO:12: Primer 6
SEQ ID NO:13: Primer 7
SEQ ID NO:14: Primer 8
SEQ ID NO:15: Primer 9
SEQ ID NO:16: Primer 10
SEQ ID NO:17: Primer 11
SEQ ID NO:18: Primer 12
SEQ ID NO:19: Primer 13
SEQ ID NO:20: Primer 14
SEQ ID NO:21: Primer 15
SEQ ID NO:22: Primer 16
SEQ ID NO:23: Primer 17
SEQ ID NO:24: Primer 18
SEQ ID NO:25: Primer 19
SEQ ID NO:26: Primer 20
SEQ ID NO:27: Primer 21
SEQ ID NO:28: Primer 22
SEQ ID NO:29: Primer 23
SEQ ID NO:30: Primer 24
SEQ ID NO:31: Primer 25
SEQ ID NO:32: Primer 26
SEQ ID NO:33: Primer 27
SEQ ID NO:34: Primer 28
SEQ ID NO:35: Primer 29
SEQ ID NO:36: Primer 30
SEQ ID NO:37: Primer 31
SEQ ID NO:38: Primer 32
SEQ ID NO:39: Primer 33

The invention claimed is:

1. A method for producing a trans-polyisoprenoid, the method comprising binding a trans-prenyltransferase (tPT) family protein to a lipid membrane in vitro, the tPT family protein being a protein obtained by deleting a membrane-binding domain from any one of the following proteins [1] to [3] and fusing a membrane-binding peptide to the resulting protein:

[1] a protein having the amino acid sequence of SEQ ID NO: 4;

[2] a protein having an amino acid sequence containing 1 to 47 amino acid substitutions, deletions, insertions, and/or additions relative to the amino acid sequence of SEQ ID NO: 4, the protein catalyzing a reaction of trans-chain elongation of an isoprenoid compound and, when a membrane-binding domain is deleted from the protein, capable of producing a product with a molecular weight of $10^4$ or more without binding to a lipid membrane; and

[3] a protein having an amino acid sequence with at least 90% sequence identity to the amino acid sequence of SEQ ID NO: 4, the protein catalyzing a reaction of trans-chain elongation of an isoprenoid compound and, when a membrane-binding domain is deleted from the protein, capable of producing a product with a molecular weight of $10^4$ or more without binding to a lipid membrane.

2. The method for producing a trans-polyisoprenoid according to claim 1, wherein the tPT family protein is a protein which has a membrane-binding domain and which can produce a product with a molecular weight of $10^4$ or more in an aqueous layer when not bound to any lipid membrane after solubilization.

3. The method for producing a trans-polyisoprenoid according to claim 1, wherein the tPT family protein is derived from a trans rubber-producing plant.

4. The method for producing a trans-polyisoprenoid according to claim 1, wherein the tPT family protein is derived from *Manilkara zapota*.

5. The method for producing a trans-polyisoprenoid according to claim 1, wherein the tPT family protein is a protein to which an ability to bind to the lipid membrane has been imparted by fusing a membrane-binding peptide to a protein having no membrane-binding domain and capable of producing a product with a molecular weight of $10^4$ or more in an aqueous layer when not bound to any lipid membrane.

6. The method for producing a trans-polyisoprenoid according to claim 5, wherein the protein having no membrane-binding domain and capable of producing a product with a molecular weight of $10^4$ or more in an aqueous layer when not bound to any lipid membrane is derived from a trans rubber-producing plant.

7. The method for producing a trans-polyisoprenoid according to claim 1, wherein the binding comprises performing protein synthesis in the presence of both the lipid membrane and a cell-free protein synthesis solution containing an mRNA coding for the tPT family protein to bind the tPT family protein to the lipid membrane.

* * * * *

```
                              SEQUENCE LISTING


Sequence total quantity: 39
SEQ ID NO: 1            moltype = DNA  length = 1263
FEATURE                 Location/Qualifiers
source                  1..1263
                        mol_type = genomic DNA
                        organism = Manilkara zapota
SEQUENCE: 1
atgttatttt ccaggggatt ttctcggatt tcgagaacca gcttgaatcg cagtcgatgc  60
ctcttttcat ttgaccacca gcatcaacta ttgattccgc ctaatcactt ctactctccg  120
agtgactcca ctgaaaaggc tttgagtggc agagataatt attccttggg ttcatttgcc  180
tttcacggca ttgcacggca attttatcac cagagcagcc ctgtagtgga ggagcaacag  240
gatccatttt cccttgttga aaatgaacta tctattcttg ctaataggtt gcggtcaatg  300
gtagttgctg aggtcccaaa gcttgcctca gctgctgagt acttcttcaa gatgggggtg  360
gaaggaaaga gatttcgacc aactgtttta ttgttgatgg caacagctct aaatgtacat  420
atacccggac caggttctaa tggggtggtt gatgttctat cgatggaact acgtaaaagg  480
caacagtgca tagctgagat aacagaaatg atccatgtgg caagccttct gcatgatgat  540
gtgttggatg atgcggatac aagacgtggc atagggtcat taaactttgt gatggggaat  600
aagttagcag tattggctgg agatttcctg ctttccagag cttgtgtggc ccttgcctct  660
ttgaagaaca cagaggttgt atcattgcta gcaactgtgg tagaacatct tgttacaggc  720
gagaccatgc aaatgagtac cacatctgat caacgttgta gcatggaata ttatttgcaa  780
aagacctact ataagactgc atcattgatt tcaaacagct gcaaagcaat tgcccttctt  840
gcagggcaaa ctgcagaggt ttcaatgttg gcttatgaat atggaaagaa tctgggattg  900
gcatatcagt taatagatga cgttctagat tttacaggca catcagcttc ccttggaaag  960
ggttctttat ctgacatccg ccatggaatt gtaactgctc caatattata tgccatcgag  1020
gagttcccac agttgcgtga agttgttgac cgaggaattg acaacactgc agatgtagat  1080
cttgttcttg attaccttgg aaaaagtcgt ggaatacaga gaacgagaga gctagcagcc  1140
aagcacgcca accttgcctc agctgcaatc gactctcttc ctgagagtga tgatgagggt  1200
gttcaaagat caaggcgagc actgttagat ctaactcaca gagtcattac aagagcaaag  1260
tag                                                               1263

SEQ ID NO: 2            moltype = AA  length = 420
FEATURE                 Location/Qualifiers
source                  1..420
                        mol_type = protein
                        organism = Manilkara zapota
SEQUENCE: 2
MLFSRGFSRI SRTSLNRSRC LFSFDHQHQL LIPPNHFYSP SDSTEKALSG RDNYSLGSFA  60
FHGIARQFYH QSSPVVEEQQ DPFSLVENEL SILANRLRSM VVAEVPKLAS AAEYFFKMGV  120
EGKRFRPTVL LLMATALNVH IPGPGSNGVV DVLSMELRKR QQCIAEITEM IHVASLLHDD  180
VLDDADTRRG IGSLNFVMGN KLAVLAGDFL LSRACVALAS LKNTEVVSLL ATVVEHLVTG  240
ETMQMSTTSD QRCSMEYYLQ KTYYKTASLI SNSCKAIALL AGQTAEVSML AYEYGKNLGL  300
AYQLIDDVLD FTGTSASLGK GSLSDIRHGI VTAPILYAIE EFPQLREVVD RGIDNTADVD  360
LVLDYLGKSR GIQRTRELAA KHANLASAAI DSLPESDDEG VQRSRRALLD LTHRVITRAK  420

SEQ ID NO: 3            moltype = DNA  length = 1422
FEATURE                 Location/Qualifiers
source                  1..1422
                        mol_type = genomic DNA
                        organism = Manilkara zapota
SEQUENCE: 3
atggccttga accttttca aaaccccatc actctttgta aaaaccttgt taaatatgtg  60
actttcttc tcatacaata ccttctgaag tttcttattg aagagaatcg agcagatttg  120
ggtacaatat ggaaagcttt aagcgcaatt ccaattccaa acagtgatcc gaaactgttc  180
aaccgtccga acaaggcagc agcgccacca ccaccgccgt tgaagaagca gttccagaag  240
gcggcaacca ccgaacactg gctgctttcg cttgtcctaa acccagtcag ttcatgtaca  300
aatctcatct ccattctcaa aagtcttgtc ctaaacccag tcagcacttc caaaaatcta  360
```

```
atcatctccc tcgtcaaaca cgttgctcag aaattcattc ctggtgaagt actcgagaag  420
aacttgctgc cgccatggtt gtcatcctca tcacctgatt caatacaccc ttctctagcc  480
catgtaatca gcaacatcaa gtccttcgag ctcgaggaca aggctttgca tggaggtgaa  540
ttcgacgaat acatggattc catgaacaaa caagtgaaca aggcactgga tggactagta  600
cccatgaagc atccagaaaa ggttcacgag gcgatgagat actccctttt agcgggtggg  660
aagcgagtgc gcccaatact gtgcattgct tcgtgccgat tggtcggcgg agacgaatca  720
tcggcgttgc caatggcgtg tgcggtggag atcattcaca ccgcttcgtt gattgtggat  780
gatcttccgt gcatggacaa cgacgatctc aggcgaggca aacccgcgag ccacaaaatg  840
tttggggaac aagtctcgat tctttccagc gctggccttt tcgctcttgc ctttcagcat  900
gtagccgctg cggagtaccc agatatggta tcagttgatc gagtgattcg aggcattgtt  960
gagctggctt cggcgttggg gacggaaggg cttgttgggg gccagtttat ggacttggat  1020
agcgaaggaa aagatattag tgagaaagaa ctagagtact tgcatgtgaa taaaacctca  1080
aagctcttgg aagcgtcggt tgtttgtgga gccatagttg gaggggctag tgaggcagat  1140
atagagaaac taaggaaata tgcgaggcta atagggttgt tgtttcaagt ggtggatgat  1200
attctggatg tcacacaatc cacagagaag ctggggaaga ctgctgccaa ggatttggtc  1260
agcaataagg ccactttccc caagcttatg ggtctcgaca atgccaagaa attcgccaac  1320
aagttggtcg aggaagccat tcaagagatt gctcactttg atgctgcaaa agctgctccg  1380
ttgtaccata tcgctcatta cattaataac cgtcaatatt aa                    1422

SEQ ID NO: 4           moltype = AA  length = 473
FEATURE                Location/Qualifiers
source                 1..473
                       mol_type = protein
                       organism = Manilkara zapota
SEQUENCE: 4
MALNLFQNPI TLCKNLVKYV TFLLIQYLLK FLIEENRADL GTIWKALSAI PIPNSDPKLF  60
NRPNKAAAPP PPPLKKQFQK AATTEHWLLS LVLNPVSSCT NLISILKSLV LNPVSTSKNL  120
IISLVKHVAQ KFIPGEVLEK NLLPPWLSSS SPDSIHPSLA HVISNIKSFE LEDKALHGGE  180
FDEYMDSMNK QVNKALDGLV PMKHPEKVHE AMRYSLLAGG KRVRPILCIA SCRLVGGDES  240
SALPMACAVE IIHTASLIVD DLPCMDNDDL RRGKPASHKM FGEQVSILSS AGLFALAFQH  300
VAAAEYPDMV SVDRVIRGIV ELASALGTEG LVGGQFMDLD SEGKDISEKE LEYLHVNKTS  360
KLLEASVVCG AIVGGASEAD IEKLRKYARL IGLLFQVVDD ILDVTQSTEK LGKTAAKDLV  420
SNKATFPKLM GLDNAKKFAN KLVEEAIQEI AHFDAAKAAP LYHIAHYINN RQY         473

SEQ ID NO: 5           moltype = DNA  length = 768
FEATURE                Location/Qualifiers
source                 1..768
                       mol_type = genomic DNA
                       note = Chlamydomonas
                       organism = unidentified
SEQUENCE: 5
atggccgagt ctgctggaaa gcctctgaag caccttgagt ttgtgcacac ctacgcgcac  60
aagtttgcga gtggtgccgc ttacgttgag ggcggctacc agaaggccaa gacctatgtt  120
cccgcggtcg ctcagcccta catcgccaaa gccgaggaga cctgcctagc atacgccgct  180
cctcttgcga caaaggcgac ggaccacgca gagaagattc tccggagcac cgacgcacag  240
ctggacgcgc tgtacgcggc ctccgccagc tggctgagca gctcccagaa gctggccgac  300
tccaacatcg cggccttcag gggcgccgcc gacaagtact acgacctggt caagtccact  360
gcgcagcacg tgacgtccaa gctgcccacc gacctgtcgg tggccaaggc ccgcgagctg  420
ctgtcggcct cgctggagca ggccaaggct ctggctgacc cggacgctgc ggtggcggcg  480
gcgctggatg cctggaccaa gttcgcagcc atcccggcgg ttgccaaggt gctgtccgcc  540
gcctccccgc tgacgggcaa gggcgtggcg gccttcacgg cggcacacga cctcctggtg  600
cactcggcgc tgtaccgcta cggcgtgtcg gtgggcgcct ccaccctggg ctgggccacc  660
agcaccaccc cctacaagtt gagcgcggct tacctgtacc cgctggtgca gcccgtggcg  720
gaccccgcgc tggacaagcg gagggccgcc gtgcaacccg gcccctag               768

SEQ ID NO: 6           moltype = DNA  length = 948
FEATURE                Location/Qualifiers
source                 1..948
                       mol_type = genomic DNA
                       organism = Manilkara zapota
SEQUENCE: 6
ctggcacatg ttattagcaa catcaaatcc tttgagctgg aagataaagc actgcatggt  60
ggtgaatttg atgagtatat ggacagcatg aacaaacagg ttaataaagc cctggatggt  120
ctggttccga tgaaacatcc ggaaaaagtt catgaagcaa tgcgttatag cctgctggca  180
ggcggtaaac gtgttcgtcc gattctgtgt attgcaagct gtcgtctggt tggtggtgat  240
gaaagcagcg cactgccgat ggcatgtgca gttgaaatta ttcataccgc aagcctgatt  300
gttgatgatc tgccgtgtat ggataatgat gacctgcgtc gtggtaaacc ggcaagccat  360
aaaatgtttg gtgaacaggt tagtattctg agcagcgcag gtctgtttgc actggcattt  420
cagcatgttg cagcagcaga atatcctgat atggttagcg ttgatcgtgt gattcgtggt  480
attgttgaac tggcaagcgc actgggcacc gaaggcctgg ttggcggtca gtttatggat  540
ctggatagcg aaggtaaaga tatcagcgaa aaagaactgg aatatctgca cgtgaacaaa  600
accagcaaac tgctggaagc aagcgttgtt tgtggtgcaa ttgttggtgg cgcaagcgaa  660
gcagatattg aaaaactgcg taaatatgcc cgtctgattg gtctgctgtt tcaggttgtg  720
gatgatattc tggatgttac ccagagcacc gaaaaactgg gcaaaaccgc agccaaagat  780
ctggttagca ataaagcaac ctttcctaaa ctgatgggcc ttgataatgc caaaaaattc  840
gccaataaac tggtggaaga ggccattcaa gaaatcgcac attttgatgc agcaaaagcc  900
gcaccgctgt atcatattgc acattatatc aataaccgcc agtattaa               948

SEQ ID NO: 7           moltype = DNA  length = 23
```

```
FEATURE                Location/Qualifiers
misc_feature           1..23
                       note = PRIMER-1
source                 1..23
                       mol_type = other DNA
                       organism = synthetic construct
SEQUENCE: 7
atgttatttt ccaggggatt ttc                                          23

SEQ ID NO: 8           moltype = DNA  length = 25
FEATURE                Location/Qualifiers
misc_feature           1..25
                       note = PRIMER-2
source                 1..25
                       mol_type = other DNA
                       organism = synthetic construct
SEQUENCE: 8
ctactttgct cttgtaatga ctctg                                        25

SEQ ID NO: 9           moltype = DNA  length = 23
FEATURE                Location/Qualifiers
misc_feature           1..23
                       note = PRIMER-3
source                 1..23
                       mol_type = other DNA
                       organism = synthetic construct
SEQUENCE: 9
cgactggagc acgaggacac tga                                          23

SEQ ID NO: 10          moltype = DNA  length = 27
FEATURE                Location/Qualifiers
misc_feature           1..27
                       note = PRIMER-4
source                 1..27
                       mol_type = other DNA
                       organism = synthetic construct
SEQUENCE: 10
cttggggaaa gtggccttat tgctgac                                      27

SEQ ID NO: 11          moltype = DNA  length = 26
FEATURE                Location/Qualifiers
misc_feature           1..26
                       note = PRIMER-5
source                 1..26
                       mol_type = other DNA
                       organism = synthetic construct
SEQUENCE: 11
ggacactgac atggactgaa ggagta                                       26

SEQ ID NO: 12          moltype = DNA  length = 27
FEATURE                Location/Qualifiers
misc_feature           1..27
                       note = PRIMER-6
source                 1..27
                       mol_type = other DNA
                       organism = synthetic construct
SEQUENCE: 12
ctgcctcact agcccctcca actatgg                                      27

SEQ ID NO: 13          moltype = DNA  length = 38
FEATURE                Location/Qualifiers
misc_feature           1..38
                       note = PRIMER-7
source                 1..38
                       mol_type = other DNA
                       organism = synthetic construct
SEQUENCE: 13
tcagggcgga tatctcgaga tggccttgaa cctttttc                          38

SEQ ID NO: 14          moltype = DNA  length = 47
FEATURE                Location/Qualifiers
misc_feature           1..47
                       note = PRIMER-8
source                 1..47
                       mol_type = other DNA
                       organism = synthetic construct
SEQUENCE: 14
ctagtgcggc cgcggtacca ttaatattga cggttattaa tgtaatg                47
```

```
SEQ ID NO: 15          moltype = DNA  length = 35
FEATURE                Location/Qualifiers
misc_feature           1..35
                       note = PRIMER-9
source                 1..35
                       mol_type = other DNA
                       organism = synthetic construct
SEQUENCE: 15
tatcgaaggt aggcatatgg aggagcaaca ggatc                             35

SEQ ID NO: 16          moltype = DNA  length = 44
FEATURE                Location/Qualifiers
misc_feature           1..44
                       note = PRIMER-10
source                 1..44
                       mol_type = other DNA
                       organism = synthetic construct
SEQUENCE: 16
cggatccctc gagggtaccc tactttgctc ttgtaatgac tctg                   44

SEQ ID NO: 17          moltype = DNA  length = 39
FEATURE                Location/Qualifiers
misc_feature           1..39
                       note = PRIMER-11
source                 1..39
                       mol_type = other DNA
                       organism = synthetic construct
SEQUENCE: 17
catatcgaag gtaggcatat gctggcacat gttattagc                         39

SEQ ID NO: 18          moltype = DNA  length = 46
FEATURE                Location/Qualifiers
misc_feature           1..46
                       note = PRIMER-12
source                 1..46
                       mol_type = other DNA
                       organism = synthetic construct
SEQUENCE: 18
cggatccctc gagggtacct taatactggc ggttattgat ataatg                 46

SEQ ID NO: 19          moltype = DNA  length = 41
FEATURE                Location/Qualifiers
misc_feature           1..41
                       note = PRIMER-13
source                 1..41
                       mol_type = other DNA
                       organism = synthetic construct
SEQUENCE: 19
catatcgaag gtaggcatat gttattttcc aggggatttt c                      41

SEQ ID NO: 20          moltype = DNA  length = 44
FEATURE                Location/Qualifiers
misc_feature           1..44
                       note = PRIMER-14
source                 1..44
                       mol_type = other DNA
                       organism = synthetic construct
SEQUENCE: 20
cggatccctc gagggtaccc tactttgctc ttgtaatgac tctg                   44

SEQ ID NO: 21          moltype = DNA  length = 25
FEATURE                Location/Qualifiers
misc_feature           1..25
                       note = PRIMER-15
source                 1..25
                       mol_type = other DNA
                       organism = synthetic construct
SEQUENCE: 21
catatgatgg ccttgaacct ttttc                                        25

SEQ ID NO: 22          moltype = DNA  length = 47
FEATURE                Location/Qualifiers
misc_feature           1..47
                       note = PRIMER-16
source                 1..47
                       mol_type = other DNA
                       organism = synthetic construct
SEQUENCE: 22
ctagtgcggc cgcggtacca ttaatattga cggttattaa tgtaatg                47
```

```
SEQ ID NO: 23           moltype = DNA  length = 29
FEATURE                 Location/Qualifiers
misc_feature            1..29
                        note = PRIMER-17
source                  1..29
                        mol_type = other DNA
                        organism = synthetic construct
SEQUENCE: 23
agtcagatat ctcatggccg agtctgctg                                    29

SEQ ID NO: 24           moltype = DNA  length = 28
FEATURE                 Location/Qualifiers
misc_feature            1..28
                        note = PRIMER-18
source                  1..28
                        mol_type = other DNA
                        organism = synthetic construct
SEQUENCE: 24
tgactggatc ctcggggccg ggttgcac                                     28

SEQ ID NO: 25           moltype = DNA  length = 24
FEATURE                 Location/Qualifiers
misc_feature            1..24
                        note = PRIMER-19
source                  1..24
                        mol_type = other DNA
                        organism = synthetic construct
SEQUENCE: 25
tgnsadgggg sggsggsggg stag                                         24

SEQ ID NO: 26           moltype = DNA  length = 34
FEATURE                 Location/Qualifiers
misc_feature            1..34
                        note = PRIMER-20
source                  1..34
                        mol_type = other DNA
                        organism = synthetic construct
SEQUENCE: 26
agtcagatat ctcatggccg agtctgctgg aaag                              34

SEQ ID NO: 27           moltype = DNA  length = 36
FEATURE                 Location/Qualifiers
misc_feature            1..36
                        note = PRIMER-21
source                  1..36
                        mol_type = other DNA
                        organism = synthetic construct
SEQUENCE: 27
ccgtcagcgg aattaccggt ggggccgggt tgcacg                            36

SEQ ID NO: 28           moltype = DNA  length = 36
FEATURE                 Location/Qualifiers
misc_feature            1..36
                        note = PRIMER-22
source                  1..36
                        mol_type = other DNA
                        organism = synthetic construct
SEQUENCE: 28
cgtgcaaccc ggccccaccg gtaattccgc tgacgg                            36

SEQ ID NO: 29           moltype = DNA  length = 31
FEATURE                 Location/Qualifiers
misc_feature            1..31
                        note = PRIMER-23
source                  1..31
                        mol_type = other DNA
                        organism = synthetic construct
SEQUENCE: 29
tgactggatc cgacccttgg gtcgatcctc c                                 31

SEQ ID NO: 30           moltype = DNA  length = 34
FEATURE                 Location/Qualifiers
misc_feature            1..34
                        note = PRIMER-24
source                  1..34
                        mol_type = other DNA
                        organism = synthetic construct
SEQUENCE: 30
```

```
agtcagatat ctcatggccg agtctgctgg aaag                          34

SEQ ID NO: 31          moltype = DNA  length = 31
FEATURE                Location/Qualifiers
misc_feature           1..31
                       note = PRIMER-25
source                 1..31
                       mol_type = other DNA
                       organism = synthetic construct
SEQUENCE: 31
tgactggatc cgacccttgg gtcgatcctc c                             31

SEQ ID NO: 32          moltype = DNA  length = 38
FEATURE                Location/Qualifiers
misc_feature           1..38
                       note = PRIMER-26
source                 1..38
                       mol_type = other DNA
                       organism = synthetic construct
SEQUENCE: 32
agtcacccgg gctagcccat gtaatcagca acatcaag                      38

SEQ ID NO: 33          moltype = DNA  length = 43
FEATURE                Location/Qualifiers
misc_feature           1..43
                       note = PRIMER-27
source                 1..43
                       mol_type = other DNA
                       organism = synthetic construct
SEQUENCE: 33
tgactgcggc cgcgttaata ttgacggtta ttaatgtaat gag                43

SEQ ID NO: 34          moltype = DNA  length = 38
FEATURE                Location/Qualifiers
misc_feature           1..38
                       note = PRIMER-28
source                 1..38
                       mol_type = other DNA
                       organism = synthetic construct
SEQUENCE: 34
agtcacccgg gctagcccat gtaatcagca acatcaag                      38

SEQ ID NO: 35          moltype = DNA  length = 43
FEATURE                Location/Qualifiers
misc_feature           1..43
                       note = PRIMER-29
source                 1..43
                       mol_type = other DNA
                       organism = synthetic construct
SEQUENCE: 35
tgactgcggc cgcgttaata ttgacggtta ttaatgtaat gag                43

SEQ ID NO: 36          moltype = DNA  length = 38
FEATURE                Location/Qualifiers
misc_feature           1..38
                       note = PRIMER-30
source                 1..38
                       mol_type = other DNA
                       organism = synthetic construct
SEQUENCE: 36
agtcacccgg gatgttattt tccaggggat tttctcgg                      38

SEQ ID NO: 37          moltype = DNA  length = 39
FEATURE                Location/Qualifiers
misc_feature           1..39
                       note = PRIMER-31
source                 1..39
                       mol_type = other DNA
                       organism = synthetic construct
SEQUENCE: 37
tgactgcggc cgcgctactt tgctcttgta atgactctg                     39

SEQ ID NO: 38          moltype = DNA  length = 30
FEATURE                Location/Qualifiers
misc_feature           1..30
                       note = PRIMER-32
source                 1..30
                       mol_type = other DNA
                       organism = synthetic construct
```

-continued

```
SEQUENCE: 38
agtcacccgg gatggccttg aaccttttc                         30

SEQ ID NO: 39          moltype = DNA  length = 43
FEATURE                Location/Qualifiers
misc_feature           1..43
                       note = PRIMER-33
source                 1..43
                       mol_type = other DNA
                       organism = synthetic construct
SEQUENCE: 39
tgactgcggc cgcgttaata ttgacggtta ttaatgtaat gag         43
```